US010835107B2

(12) United States Patent
Terliuc et al.

(10) Patent No.: US 10,835,107 B2
(45) Date of Patent: Nov. 17, 2020

(54) ENDOSCOPE ELECTRO-PNEUMATIC ADAPTOR

(71) Applicant: SMART MEDICAL SYSTEMS LTD., Ra'anana (IL)

(72) Inventors: Gad Terliuc, Ra'anana (IL); Gilad Luria, Givatayim (IL); Amnon Potash, Kibbutz Shefayim (IL)

(73) Assignee: SMART MEDICAL SYSTEMS LTD., Raanana (IL)

( * ) Notice: Subject to any disclaimer, the term of this patent is extended or adjusted under 35 U.S.C. 154(b) by 210 days.

(21) Appl. No.: 15/562,439

(22) PCT Filed: Mar. 31, 2016

(86) PCT No.: PCT/IL2016/050345
§ 371 (c)(1),
(2) Date: Sep. 28, 2017

(87) PCT Pub. No.: WO2016/157189
PCT Pub. Date: Oct. 6, 2016

(65) Prior Publication Data
US 2018/0084973 A1 Mar. 29, 2018

Related U.S. Application Data

(60) Provisional application No. 62/178,207, filed on Apr. 3, 2015.

(51) Int. Cl.
*A61B 1/00* (2006.01)
*A61B 1/12* (2006.01)
(Continued)

(52) U.S. Cl.
CPC ...... *A61B 1/00057* (2013.01); *A61B 1/00082* (2013.01); *A61B 1/00124* (2013.01);
(Continued)

(58) Field of Classification Search
CPC ........ A61M 25/1018; A61M 25/10181; A61M 25/10184; A61M 25/1025; A61M 3/02;
(Continued)

(56) References Cited

U.S. PATENT DOCUMENTS 3,837,347 A   9/1974   Tower
3,895,637 A   7/1975   Choy
(Continued)

FOREIGN PATENT DOCUMENTS

CA   2661242   10/2010
CN   1394543   2/2003
(Continued)

OTHER PUBLICATIONS

An International Search Report and a Written Opinion both dated Sep. 4, 2014, which issued during the prosecution of Applicant's PCT/IL2014/000025.
(Continued)

*Primary Examiner* — Ryan N Henderson
(74) *Attorney, Agent, or Firm* — AlphaPatent Associates, Ltd; Daniel J. Swirsky

(57) ABSTRACT

An endoscope system including an endoscope including an endoscope electro-pneumatic connection assembly having a leak test port, an endoscope electro-optic subsystem which is connectable to the endoscope via the endoscope electro-pneumatic connection assembly in a manner which precludes access to the leak test port when the endoscope electro-optic subsystem and the endoscope are connected at the electro-pneumatic connection assembly and an electro-pneumatic adaptor, which is connectable to the endoscope at the electro-pneumatic connection assembly and includes an adaptor electro-pneumatic connection assembly, including a leak test port connector for connection to the leak test port of the endoscope, an adaptor electrical port assembly to
(Continued)

which the endoscope electro-optic subsystem is connectable and a pneumatic port.

8 Claims, 21 Drawing Sheets

(51) Int. Cl.
  *A61B 90/70* (2016.01)
  *A61M 25/10* (2013.01)
(52) U.S. Cl.
  CPC ...... *A61B 1/00126* (2013.01); *A61B 1/00128* (2013.01); *A61B 1/12* (2013.01); *A61B 90/70* (2016.02); *A61B 2090/701* (2016.02); *A61M 25/1018* (2013.01)
(58) Field of Classification Search
  CPC ..... A61M 3/04; A61M 3/007; A61B 1/00057; A61B 1/00059; A61B 1/00062; A61B 1/00066; A61B 1/00082; A61B 1/015; A61B 1/00112; A61B 1/00114; A61B 1/00117; A61B 1/00119; A61B 1/00121; A61B 1/00124; A61B 1/00126; A61B 1/00128; A61B 90/70; A61B 2090/701
  See application file for complete search history.

(56) References Cited

U.S. PATENT DOCUMENTS

| | | |
|---|---|---|
| 4,040,413 A | 8/1977 | Ohshiro |
| 4,148,307 A | 4/1979 | Utsugi |
| 4,176,662 A | 12/1979 | Frazer |
| 4,195,637 A | 4/1980 | Gruntzig et al. |
| 4,224,929 A | 9/1980 | Furihata |
| 4,261,339 A | 4/1981 | Hanson et al. |
| 4,453,545 A | 6/1984 | Inoue |
| 4,616,652 A | 10/1986 | Simpson |
| 4,676,228 A | 6/1987 | Krasner et al. |
| 4,681,093 A | 7/1987 | Ono et al. |
| 4,690,131 A | 9/1987 | Lyddy et al. |
| 4,721,123 A | 1/1988 | Cosentino et al. |
| 4,862,874 A | 9/1989 | Kellner |
| 4,917,088 A | 4/1990 | Crittenden |
| 5,135,487 A | 8/1992 | Morrill et al. |
| 5,259,366 A | 11/1993 | Reydel et al. |
| 5,310,524 A | 5/1994 | Campbell et al. |
| 5,338,299 A | 8/1994 | Barlow |
| 5,411,016 A | 5/1995 | Kume et al. |
| 5,454,364 A | 10/1995 | Kruger |
| 5,569,220 A | 10/1996 | Webster, Jr. |
| 5,593,419 A | 1/1997 | Segar |
| 5,599,301 A | 2/1997 | Jacobs et al. |
| 5,607,441 A | 3/1997 | Sierocuk et al. |
| 5,653,240 A | 8/1997 | Zimmon |
| 5,693,014 A | 12/1997 | Abele |
| 5,700,242 A | 12/1997 | Mulder |
| 5,707,382 A | 1/1998 | Sierocuk et al. |
| 5,707,392 A | 1/1998 | Kortenbach |
| 5,823,940 A | 10/1998 | Newman |
| 5,904,701 A | 5/1999 | Daneshvar |
| 5,984,860 A | 11/1999 | Shan |
| 6,007,482 A | 12/1999 | Madni et al. |
| 6,162,171 A | 12/2000 | Ng et al. |
| 6,261,260 B1 | 7/2001 | Maki et al. |
| 6,412,334 B1 | 7/2002 | Kral et al. |
| 6,461,294 B1 | 10/2002 | Oneda et al. |
| 6,585,639 B1 | 7/2003 | Kotmel et al. |
| 6,589,208 B2 | 7/2003 | Ewers et al. |
| 6,663,589 B1 | 12/2003 | Halevy |
| 6,695,810 B2 | 2/2004 | Peacock |
| 6,702,735 B2 | 3/2004 | Kelly |
| 6,764,441 B2 | 7/2004 | Chiel |
| 6,986,736 B2 | 1/2006 | Williams et al. |
| 7,081,096 B2 | 7/2006 | Brister et al. |
| 7,169,140 B1 | 1/2007 | Kume |
| 7,635,346 B2 | 12/2009 | Cabiri et al. |
| 7,695,428 B2 | 4/2010 | Machida |
| 7,699,771 B2 | 4/2010 | Wendlandt |
| 7,713,191 B2 | 5/2010 | Sekiguchi et al. |
| 7,837,672 B2 | 11/2010 | Intoccia |
| 7,887,480 B2 | 2/2011 | Sekiguchi |
| 7,918,788 B2 | 4/2011 | Lin et al. |
| 7,963,911 B2 | 6/2011 | Terliuc |
| 8,002,698 B2 | 8/2011 | Motai |
| 8,012,084 B2 | 9/2011 | Machida |
| 8,152,715 B2 | 4/2012 | Root et al. |
| 8,187,221 B2 | 5/2012 | Bates |
| 8,197,463 B2 | 6/2012 | Intoccia |
| 8,273,013 B2 | 9/2012 | Niwa et al. |
| 8,348,889 B2 | 1/2013 | Salemi et al. |
| 8,419,678 B2 | 4/2013 | Cabiri et al. |
| 8,480,572 B2 | 7/2013 | Ishigami |
| 8,545,382 B2 | 10/2013 | Suzuki et al. |
| 8,727,970 B2 | 5/2014 | Terliuc et al. |
| 8,939,895 B2 | 1/2015 | Simchony |
| 9,119,532 B2 | 9/2015 | Terliuc et al. |
| 9,511,209 B2 | 1/2016 | Drasler |
| 9,278,202 B2 | 3/2016 | Ranade |
| 9,427,142 B2 | 8/2016 | Terliuc et al. |
| 9,480,390 B2 | 11/2016 | Farhadi |
| 9,521,945 B2 | 12/2016 | Farhadi |
| 9,596,979 B2 | 3/2017 | Terliuc et al. |
| 9,604,042 B2 | 3/2017 | Fox |
| 9,661,994 B2 | 5/2017 | Terliuc et al. |
| 9,795,280 B2 | 10/2017 | Ueda |
| 9,808,142 B2 | 11/2017 | Axon et al. |
| 2001/0032494 A1 | 10/2001 | Greszler |
| 2002/0147385 A1 | 10/2002 | Butler et al. |
| 2003/0074015 A1 | 4/2003 | Nakao |
| 2003/0236495 A1 | 12/2003 | Kennedy |
| 2004/0077926 A1 | 4/2004 | Moriyama |
| 2004/0102681 A1 | 5/2004 | Gross |
| 2004/0210116 A1 | 10/2004 | Nakao |
| 2004/0236366 A1 | 11/2004 | Kennedy et al. |
| 2005/0027253 A1 | 2/2005 | Castellano et al. |
| 2005/0124856 A1 | 6/2005 | Fujikura et al. |
| 2005/0125005 A1 | 6/2005 | Fujikura |
| 2005/0133453 A1 | 6/2005 | Woodruff et al. |
| 2005/0137457 A1 | 6/2005 | Machida |
| 2005/0159702 A1 | 7/2005 | Sekiguchi et al. |
| 2005/0165233 A1 | 7/2005 | Hamedi et al. |
| 2005/0165273 A1 | 7/2005 | Takano |
| 2005/0171400 A1 | 8/2005 | Itoi |
| 2006/0095063 A1 | 5/2006 | Sekiguchi |
| 2006/0100480 A1 | 5/2006 | Ewers et al. |
| 2006/0111610 A1 | 5/2006 | Machida |
| 2006/0116549 A1 | 6/2006 | Sekiguchi et al. |
| 2006/0161044 A1 | 7/2006 | Oneda et al. |
| 2006/0282088 A1 | 12/2006 | Ryan |
| 2007/0010785 A1 | 1/2007 | Sekiguchi et al. |
| 2007/0038026 A1 | 2/2007 | Yoshida et al. |
| 2007/0083158 A1 | 4/2007 | Hirszowicz et al. |
| 2007/0185385 A1 | 8/2007 | Noguchi et al. |
| 2007/0191678 A1 | 8/2007 | Sekiguchi |
| 2007/0213586 A1 | 9/2007 | Hirose et al. |
| 2007/0244361 A1 | 10/2007 | Ikeda et al. |
| 2007/0270645 A1 | 11/2007 | Ikeda |
| 2007/0276181 A1 | 11/2007 | Terliuc |
| 2008/0009673 A1 | 1/2008 | Khachi |
| 2008/0161645 A1 | 7/2008 | Goldwasser et al. |
| 2008/0177142 A1 | 7/2008 | Roskopf |
| 2008/0200759 A1 | 8/2008 | Niwa et al. |
| 2008/0306441 A1 | 12/2008 | Brown et al. |
| 2009/0012469 A1 | 1/2009 | Nita |
| 2009/0018500 A1 | 1/2009 | Carter et al. |
| 2009/0048483 A1 | 2/2009 | Yamamoto |
| 2009/0156896 A1 | 6/2009 | Kura |
| 2009/0187069 A1 | 7/2009 | Terliuc et al. |
| 2009/0234188 A1 | 9/2009 | Matsuura et al. |
| 2009/0287058 A1 | 11/2009 | Terliuc |
| 2010/0041951 A1 | 2/2010 | Glozman et al. |
| 2010/0042046 A1 | 2/2010 | Chang et al. |

(56) References Cited

U.S. PATENT DOCUMENTS

| | | |
|---|---|---|
| 2010/0217185 A1 | 8/2010 | Terliuc et al. |
| 2012/0178994 A1 | 7/2012 | Schembre |
| 2012/0232342 A1 | 9/2012 | Reydel |
| 2012/0285488 A1 | 11/2012 | Labib et al. |
| 2013/0023920 A1 | 1/2013 | Terliuc et al. |
| 2013/0090527 A1 | 4/2013 | Axon |
| 2013/0116549 A1 | 5/2013 | Gunday |
| 2013/0197309 A1* | 8/2013 | Sakata ............... A61B 1/00124 600/132 |
| 2014/0088362 A1 | 3/2014 | Terliuc et al. |
| 2014/0155696 A1 | 6/2014 | Sakata |
| 2015/0073216 A1 | 3/2015 | Papay |
| 2015/0273191 A1 | 10/2015 | Terliuc et al. |
| 2015/0335229 A1 | 11/2015 | Terliuc |
| 2016/0022120 A1 | 1/2016 | Terliuc et al. |
| 2016/0081536 A1 | 3/2016 | Farhadi |
| 2016/0089001 A1 | 3/2016 | Hara et al. |
| 2016/0095508 A1 | 4/2016 | Terliuc et al. |
| 2017/0014099 A1 | 1/2017 | Morimoto |
| 2017/0027415 A1 | 2/2017 | Terliuc et al. |
| 2017/0027433 A1 | 2/2017 | Terliuc |
| 2017/0065155 A1 | 3/2017 | Farhadi |
| 2017/0216568 A1 | 3/2017 | Terliuc et al. |
| 2017/0100017 A1 | 4/2017 | Terliuc et al. |
| 2017/0106173 A1 | 4/2017 | Chanduszko |
| 2017/0181606 A1* | 6/2017 | Waagen ............. A61B 1/00121 |
| 2017/0203080 A1 | 7/2017 | Terliuc et al. |
| 2017/0360282 A1 | 12/2017 | Terliuc et al. |
| 2018/0125606 A1* | 5/2018 | Labib ...................... C12Q 1/06 |
| 2018/0140175 A1* | 5/2018 | Luria ..................... A61B 1/125 |
| 2018/0333043 A1 | 11/2018 | Terliuc et al. |

FOREIGN PATENT DOCUMENTS

| | | |
|---|---|---|
| CN | 2624936 | 7/2004 |
| CN | 1550203 | 12/2004 |
| CN | 1636502 | 7/2005 |
| CN | 1647747 | 8/2005 |
| CN | 1649630 | 8/2005 |
| CN | 1827031 | 9/2006 |
| CN | 1917802 | 2/2007 |
| CN | 1933766 | 3/2007 |
| CN | 1946328 | 4/2007 |
| CN | 1951312 | 4/2007 |
| CN | 1964665 | 5/2007 |
| CN | 101015440 | 8/2007 |
| CN | 101103898 | 1/2008 |
| CN | 101243965 | 8/2008 |
| CN | 101347321 | 1/2009 |
| CN | 101380220 | 3/2009 |
| CN | 101396256 | 4/2009 |
| CN | 101522091 | 9/2009 |
| CN | 101541227 | 9/2009 |
| CN | 101664560 | 3/2010 |
| CN | 102791180 | 11/2012 |
| CN | 103269638 | 8/2013 |
| DE | 4317601 A1 | 12/1994 |
| DE | 10209993 A1 | 4/2003 |
| EP | 0 212 696 | 3/1987 |
| EP | 0473045 A1 | 3/1992 |
| EP | 0733342 | 9/1996 |
| EP | 1433410 | 6/2004 |
| EP | 1547641 | 6/2005 |
| EP | 1550465 A1 | 7/2005 |
| EP | 1656879 | 5/2006 |
| EP | 1666864 A1 | 6/2006 |
| EP | 1707221 A1 | 10/2006 |
| EP | 1556118 B1 | 12/2006 |
| EP | 2108303 A1 | 10/2009 |
| EP | 1726248 B1 | 12/2010 |
| EP | 1335659 B1 | 4/2011 |
| EP | 1551316 B1 | 8/2011 |
| EP | 2110068 B1 | 8/2011 |
| EP | 2764818 A1 | 8/2014 |
| EP | 1706169 B1 | 5/2015 |
| EP | 2320984 B1 | 10/2015 |
| JP | S48-068542 | 6/1973 |
| JP | SHO50-016762 | 2/1975 |
| JP | JPS57-57804 | 4/1982 |
| JP | S62-002925 | 6/1985 |
| JP | SHO61-284226 | 12/1986 |
| JP | SHO62-002925 | 1/1987 |
| JP | S61-202274 | 7/1988 |
| JP | SHO63-102429 | 7/1988 |
| JP | SHO64-017203 | 1/1989 |
| JP | H2-58402 | 4/1990 |
| JP | H04-102436 | 4/1992 |
| JP | H04-297219 | 10/1992 |
| JP | HEI 05337081 | 12/1993 |
| JP | H06-63045 | 3/1994 |
| JP | HEI6-339455 | 12/1994 |
| JP | HEI7-12101 | 2/1995 |
| JP | HEI7-148105 | 6/1995 |
| JP | H08228996 | 9/1996 |
| JP | HEI10-127571 | 5/1998 |
| JP | HEI 10-286223 | 10/1998 |
| JP | HEI10-286309 | 10/1998 |
| JP | HEI11-225947 | 8/1999 |
| JP | 2000-060793 | 2/2000 |
| JP | 2000-189385 | 7/2000 |
| JP | 2000-329534 | 11/2000 |
| JP | 2002-34900 | 2/2002 |
| JP | 2002-301019 | 10/2002 |
| JP | 2003-275173 | 9/2003 |
| JP | 2003250896 | 9/2003 |
| JP | 2004-97718 | 4/2004 |
| JP | 2004-329720 | 11/2004 |
| JP | 2005-185704 | 7/2005 |
| JP | 2005-185706 | 7/2005 |
| JP | 2005-185707 | 7/2005 |
| JP | 2005-205181 | 8/2005 |
| JP | 2005-279128 | 10/2005 |
| JP | 2005296256 | 10/2005 |
| JP | 2005-334475 | 12/2005 |
| JP | 2006-130014 | 5/2006 |
| JP | 2006-167310 | 6/2006 |
| JP | 2006-304906 | 11/2006 |
| JP | 2006-334149 | 12/2006 |
| JP | 2007-014475 | 1/2007 |
| JP | 2007-026814 | 2/2007 |
| JP | 2007-130082 | 5/2007 |
| JP | 2007-517576 | 7/2007 |
| JP | 2007-521907 | 8/2007 |
| JP | 2007-268137 | 10/2007 |
| JP | 2007-268147 | 10/2007 |
| JP | 2007-296054 | 11/2007 |
| JP | 2008-006000 | 1/2008 |
| JP | 2008125886 | 6/2008 |
| JP | 2008-537493 | 9/2008 |
| JP | 2009-056121 | 3/2009 |
| JP | 2009-195321 | 9/2009 |
| JP | 2009-537212 | 10/2009 |
| JP | 2009-254554 | 11/2009 |
| JP | 2012504431 | 4/2010 |
| WO | 96/00099 | 1/1996 |
| WO | 98/30249 | 7/1998 |
| WO | 02/094087 | 11/2002 |
| WO | 2005/017854 | 2/2005 |
| WO | 2005/074377 | 8/2005 |
| WO | 2005/089625 | 9/2005 |
| WO | WO2006123590 A1 | 11/2006 |
| WO | 2007/023492 | 3/2007 |
| WO | 2007/135665 | 11/2007 |
| WO | 2008/004228 | 1/2008 |
| WO | WO2008073126 A1 | 6/2008 |
| WO | WO2008121143 A1 | 10/2008 |
| WO | 2008/142685 | 11/2008 |
| WO | 2009/122395 | 10/2009 |
| WO | 2010/046891 | 4/2010 |
| WO | WO2010070291 A2 | 6/2010 |
| WO | 2010/137025 | 12/2010 |
| WO | 2011/111040 | 9/2011 |
| WO | 2014/188402 | 11/2014 |

(56) References Cited

FOREIGN PATENT DOCUMENTS

| WO | WO2014188402 A1 | 11/2014 |
|---|---|---|
| WO | WO2015160970 A1 | 10/2015 |
| WO | WO2016103247 A1 | 6/2016 |
| WO | WO2017004432 A1 | 1/2017 |

OTHER PUBLICATIONS

An International Preliminary Report on Patentability dated Nov. 24, 2015, which issued during the prosecution of Applicant's PCT/IL2014/000025.
European Search Report dated Jan. 4, 2017, which issued during the prosecution of Applicant's European App No. 14800390.8.
An Office Action dated Dec. 9, 2016, which issued during the prosecution of Chinese Patent Application No. 201480029252.5.
European Search Report dated Apr. 8, 2014, which issued during the prosecution of Applicant's European App No. 11752941.2.
An Office Action dated May 25, 2016, which issued during the prosecution of Chinese Patent Application No. 201410483767.9.
An International Search Report and a Written Opinion both dated Oct. 18, 2011 which issued during the prosecution of Applicant's PCT/IL2011/000222.
An International Preliminary Report on Patentability dated Sep. 11, 2012, which issued during the prosecution of Applicant's PCT/IL2011/000222.
An Office Action dated Mar. 16, 2017, which issued during the prosecution of Chinese Patent Application No. 201410483767.9.
An Office Action dated Jun. 25, 2015, which issued during the prosecution of U.S. Appl. No. 13/583,634.
An Office Action dated Apr. 3, 2015, which issued during the prosecution of Japanese Patent Application No. 2012-556642.
An Office Action dated Sep. 16, 2016, which issued during the prosecution of Japanese Patent Application No. 2015-175589.
An Office Action dated Feb. 11, 2015, which issued during the prosecution of Chinese Patent Application No. 2011/0013002.9.
An Office Action dated Aug. 4, 2014, which issued during the prosecution of Chinese Patent Application No. 2011/0013002.9.
An Office Action dated Feb. 22, 2017, which issued during the prosecution of U.S. Appl. No. 13/583,634.
An Office Action dated Apr. 4, 2014, which issued during the prosecution of U.S. Appl. No. 13/583,634.
An Office Action dated Nov. 5, 2014, which issued during the prosecution of U.S. Appl. No. 13/583,634.
An Office Action dated Jun. 14, 2016, which issued during the prosecution of U.S. Appl. No. 13/583,634.
Notice of Allowance dated May 28, 2015, which issued during the prosecution of Chinese Patent Application No. 2011/0013002.9.
An Office Action dated May 24, 2016, which issued during the prosecution of Chinese Patent Application No. 201510483997.5.
An Office Action dated Jul. 20, 2016, which issued during the prosecution of Chinese Patent Application No. 201510483785.7.
An Office Action dated May 24, 2017, which issued during the prosecution of Chinese Patent Application No. 201510483785.7.
An Office Action dated Jun. 3, 2016, which issued during the prosecution of Chinese Patent Application No. 201410484557.1.
An Office Action dated Mar. 15, 2017, which issued during the prosecution of Chinese Patent Application No. 201410484557.1.
An Office Action dated Jun. 1, 2016, which issued during the prosecution of Chinese Patent Application No. 201510484559.0.
An Office Action dated Mar. 20, 2017, which issued during the prosecution of Chinese Patent Application No. 201510483997.5.
An Office Action dated Mar. 20, 2017, which issued during the prosecution of Chinese Patent Application No. 201510484559.0.
An Office Action dated Apr. 25, 2016, which issued during the prosecution of Chinese Patent Application No. 201510484558.6.
Notice of Allowance dated Mar. 10, 2017, which issued during the prosecution of Chinese Patent Application No. 201510484558.6.
An International Search Report and a Written Opinion both dated Jul. 13, 2012, which issued during the prosecution of Applicant's PCT/IL12/00003.
An International Preliminary Report on Patentability dated Sep. 10, 2013, which issued during the prosecution of Applicant's PCT/IL12/00003.
An Office Action dated Mar. 13, 2017, which issued during the prosecution of Chinese Patent Application No. 201510484566.0.
An Office Action dated Apr. 25, 2016, which issued during the prosecution of Chinese Patent Application No. 201510484566.0.
An Office Action dated Feb. 1, 2016, which issued during the prosecution of Australian Patent Application No. 2011225671.
Notice of Allowance dated Feb. 10, 2017, which issued during the prosecution of Australian Patent Application No. 2011225671.
Single Balloon Endoscope: Balloon pump control OBCU: http://medical.olympusamerica.com/products/control/ballooncontrol-unit-obcu,[online].
Single Balloon Endoscope: SIF-Q 1 80 enteroscope: http://medical.olympusamerica.com/products/enteroscope/evisexera-ii-sif-q180,[online].
An Office Action dated Jan. 21, 2016, which issued during the prosecution of Canadian Patent Application No. 2,791,838.
European Search Report dated Jul. 16, 2014, which issued during the prosecution of Applicant's European App No. 12754885.7.
EVIS EXERA II CLV-180 product brochure, http://www.olympus.nl/medical/en/medical_systems/hidden/downloadJsp.jsp?link=/medical/rmt/media/content/content 1/documents 1/brochures 1/EVIS_EXERA_11_CLV-180_product_brochure_001_V1-en_GB_20000101.pdf, [online].
BS-2 Front Balloon, http://www.fujifilmusa.com/products/medical/endoscopy/endoscopes/specialized-balloons-andovertube/index.html#balloonsspecifications, [online].
An Office Action dated Jan. 30, 2017, which issued during the prosecution of Canadian Patent Application No. 2,791,838.
Double Balloon Endoscope: EC-450B15 colonoscope: http://www.fujifilmusa.com/products.medical/endoscopy/endoscopes/enteroscopes/index.html,[online].
Double Balloon Endoscope: Balloon pump controller BP-30: http://www.fujifilmusa.com/products/medical/endoscopy/endoscopes/balloon-pump-controller/index.html,[online].
Double Balloon Endoscope: EPX-4440HD video system: http://www.fujifilmusa.com/products/medical/endoscopy/video-systems/epx-4440hd, [online].
Double Balloon Endoscope: TS-13 101 overtube: http://www.fujifilmusa.com/products/medical/endoscopy/endoscopes/specialized-balloons-and-overtube/index.html,[online].
Single Balloon Endoscope: ST-SB 1 overtube: http://medical.olympusamerica.com/products/tubes/single-use-st-sb 11, [online].
U.S. Appl. No. 61/855,688, filed May 21, 2013.
U.S. Appl. No. 61/962,383, filed Nov. 6, 2013.
A communication from the European Patent Office dated Jul. 23, 2015, which issued during the prosecution of European Application No. 12754885.7.
An Office Action dated Nov. 22, 2016, which issued during the prosecution of U.S. Appl. No. 13/583,634.
An Office Action dated Mar. 18, 2015, which issued during the prosecution of U.S. Appl. No. 13/583,634.
An Office Action dated May 9, 2016, which issued during the prosecution of U.S. Appl. No. 13/583,634.
An Office Action dated Oct. 7, 2015, which issued during the prosecution of U.S. Appl. No. 13/583,634.
An Office Action dated Mar. 28, 2017, which issued during the prosecution of U.S. Appl. No. 13/583,634.
A communication from the European Patent Office dated Jul. 6, 2016, which issued during the prosecution of European Application No. 12754885.7.
A communication from the European Patent Office dated May 17, 2017, which issued during the prosecution of European Application No. 12754885.7.
An Office Action dated Apr. 15, 2016, which issued during the prosecution of Chinese Patent Application No. 201280022024.6.
An Office Action dated May 26, 2015, which issued during the prosecution of Chinese Patent Application No. 201280022024.6.

(56) References Cited

OTHER PUBLICATIONS

An Office Action dated Nov. 1, 2016, which issued during the prosecution of Chinese Patent Application No. 201280022024.6.
An Office Action dated Dec. 9, 2016, which issued during the prosecution of Australian Patent Application No. 2012226390.
Notice of Allowance dated Dec. 22, 2016, which issued during the prosecution of Australian Patent Application No. 2012226390.
An Office Action dated Oct. 27, 2015, which issued during the prosecution of Japanese Patent Application No. 2013-557219.
An Office Action dated Oct. 24, 2016, which issued during the prosecution of Japanese Patent Application No. 2013-557219.
An Office Action dated Dec. 28, 2015, which issued during the prosecution of Japanese Patent Application No. 2015-004799.
An Office Action dated Dec. 6, 2016, which issued during the prosecution of Japanese Patent Application No. 2015-004799.
An Office Action dated Dec. 15, 2015, which issued during the prosecution of Australian Patent Application No. 2012226390.
An Office Action dated Sep. 3, 2015, which issued during the prosecution of Israel Patent Application No. 221621.
An Office Action dated Nov. 14, 2016, which issued during the prosecution of Israel Patent Application No. 228174.
An Office Action dated Jul. 5, 2017, which issued during the prosecution of Chinese Patent Application No. 201280022024.6.
An Office Action dated Jul. 18, 2017, which issued during the prosecution of Canadian Patent Application No. 2,828,608.
An Office Action dated Jul. 24, 2017, which issued during the prosecution of Japanese Patent Application No. 2012-556642.
A Notice of Allowance dated Aug. 24, 2017, which issued during the prosecution of Chinese Patent Application No. 201510484557.1.
An Office Action dated Sep. 18, 2017, which issued during the prosecution of U.S. Appl. No. 14/891,683.
Notice of Allowance in Chinese Patent App. No. 201510483785.7, dated Sep. 26, 2017.
Office Action in Chinese Patent App. No. 201510484566.0, dated Oct. 20, 2017.
Notice of Allowance in Chinese Patent App. No. 201510484557.1, dated Aug. 24, 2017.
Office Action in Chinese Patent App. No. 201510483767.9, dated Nov. 27, 2017.
Office Action in Chinese Patent App. No. 201510484559.0, dated Dec. 14, 2017.
Decision of Rejection in Chinese Patent App. No. 201510483997.5, dated Sep. 28, 2017.
Office Action in Chinese Patent App. No. 201480029252.5, dated Nov. 1, 2017.
Office Action in Australian Patent App. No. 2014269901, dated Jan. 12, 2018.
Office Action in Australian Patent App. No. 2017202285, dated Jan. 4, 2018.
Office Action in Canadian Patent App. No. 2,791,838, dated Dec. 15, 2017.
Final Rejection in U.S. Appl. No. 14/003,799, dated Oct. 5, 2017.
Non Final Rejection in U.S. Appl. No. 14/891,683, dated Sep. 18, 2017.
Office Action in JP 2016189043 dated Jul. 24, 2017.
Office Action in EP 11752941.2 dated Feb. 6, 2018.
Office Action in U.S. Appl. No. 14/003,799 dated Oct. 5, 2017.
Office Action in U.S. Appl. No. 14/003,799 dated Mar. 27, 2018.
Office Action in JP 2017012628 dated Feb. 26, 2018.
Office Action in JP 2016514529 dated Feb. 9, 2018.
International Preliminary Report on Patentability in WO/2016/157189 dated Oct. 3, 2017.
International Search Report in WO/2016/157189 dated Sep. 7, 2016.
Written Opinion of the International Search Authority in WO/2016/157189 dated Sep. 7, 2016.
International Search Report in WO/2016/103247 dated Mar. 17, 2016.
Written Opinion of the International Search Authority in WO/2016/103247 dated Mar. 17, 2016.
International Preliminary Report on Patentability in WO/2016/103247 dated Jun. 27, 2017.

* cited by examiner

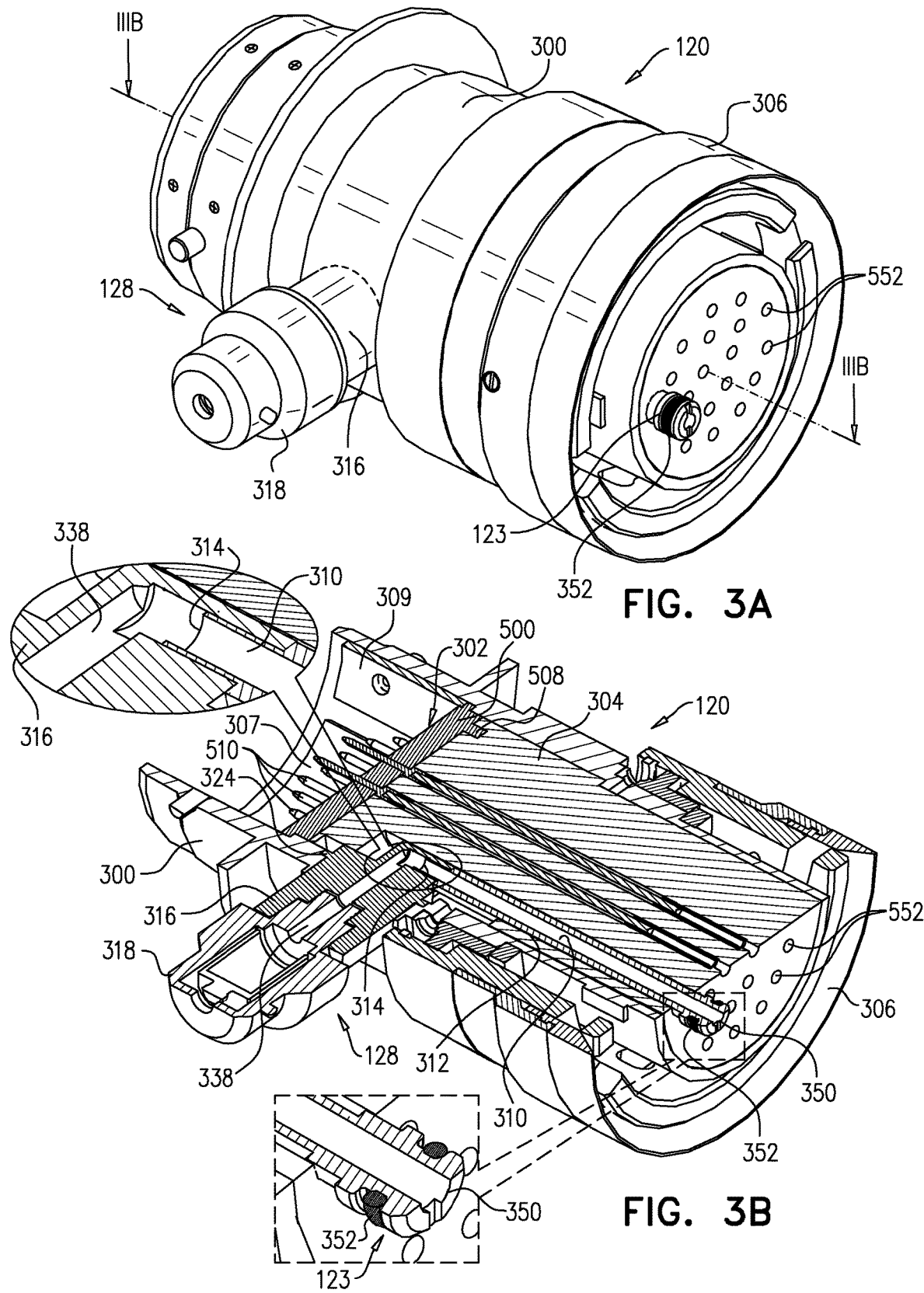

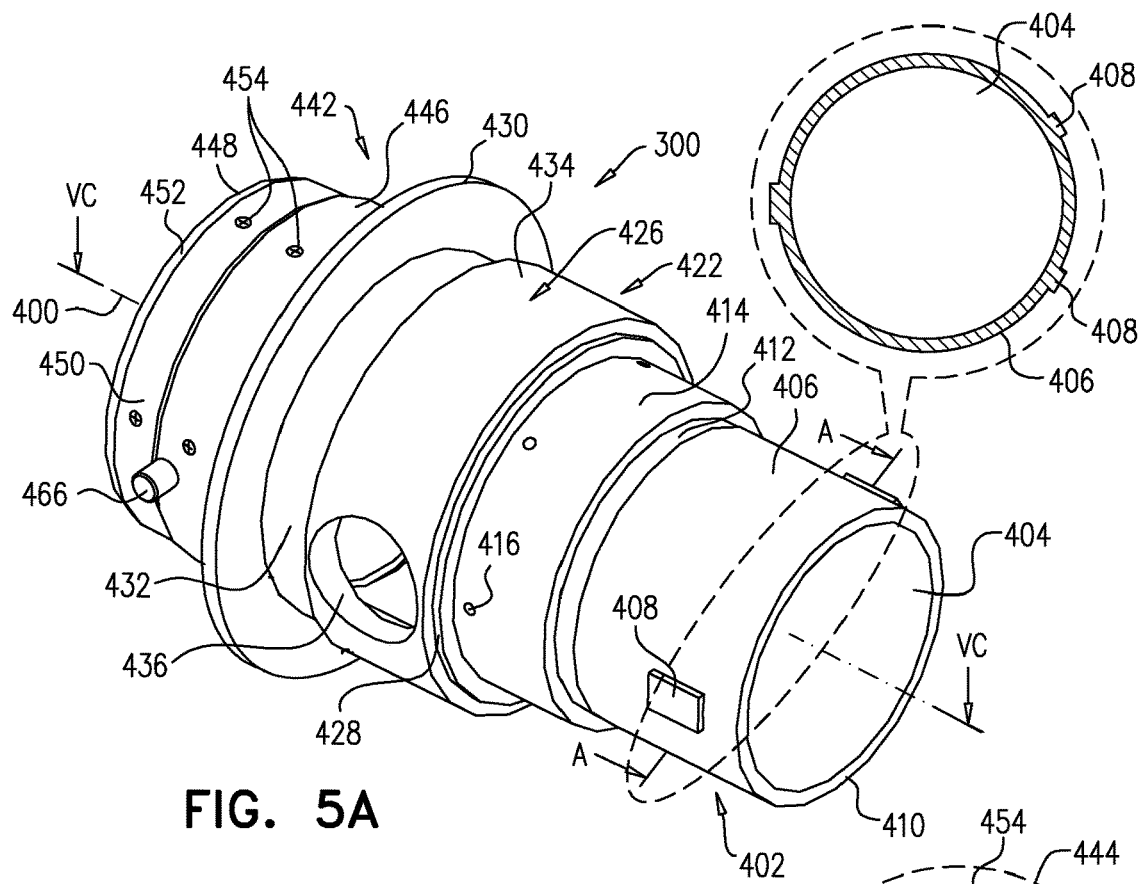
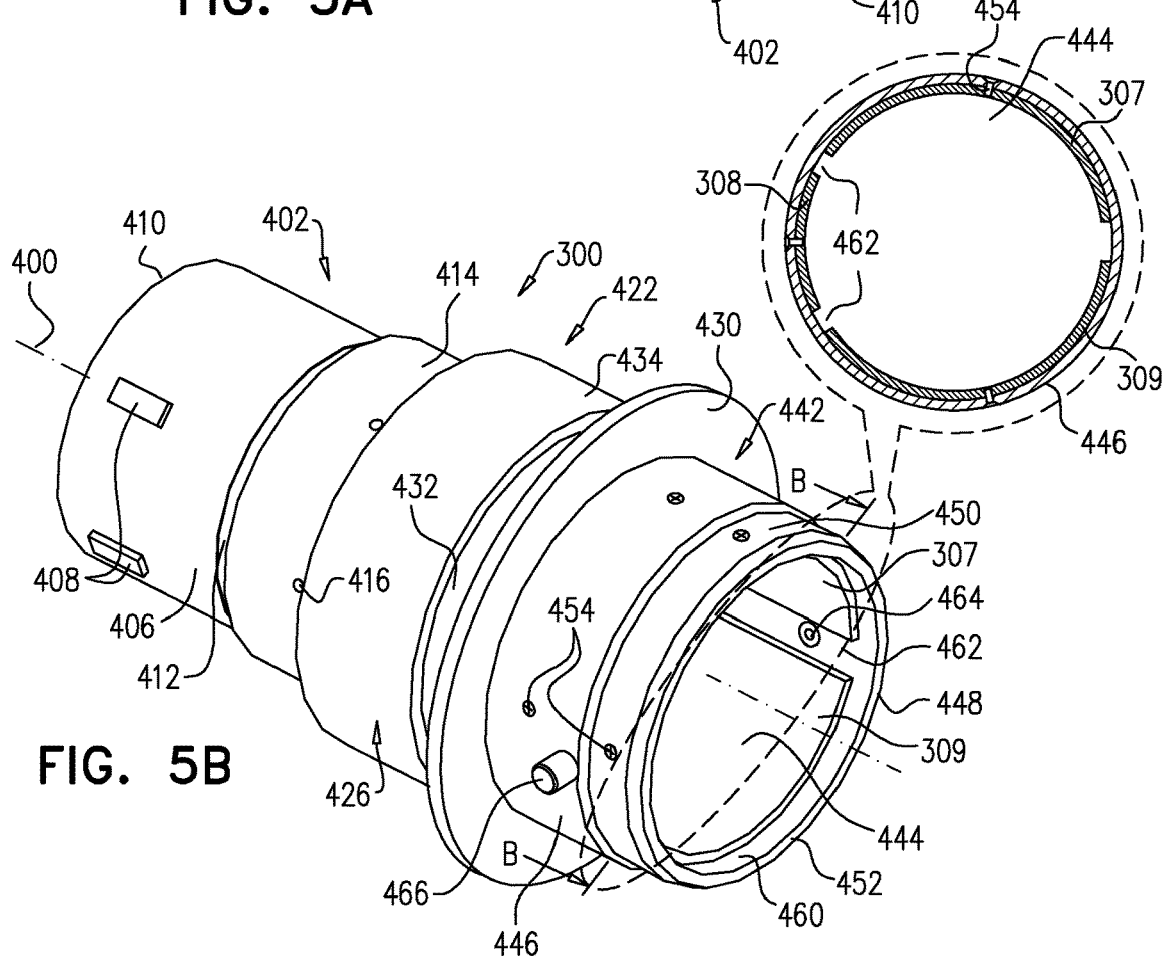
FIG. 5A
FIG. 5B

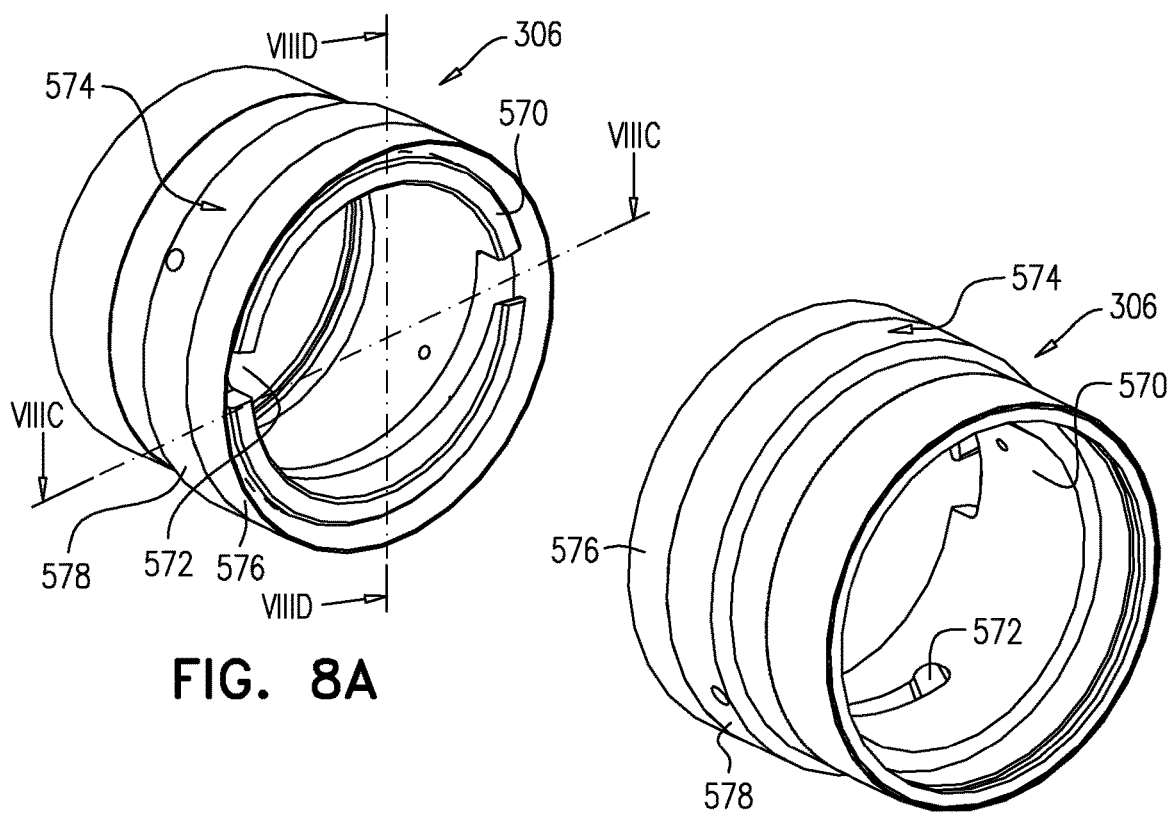
FIG. 8A
FIG. 8B
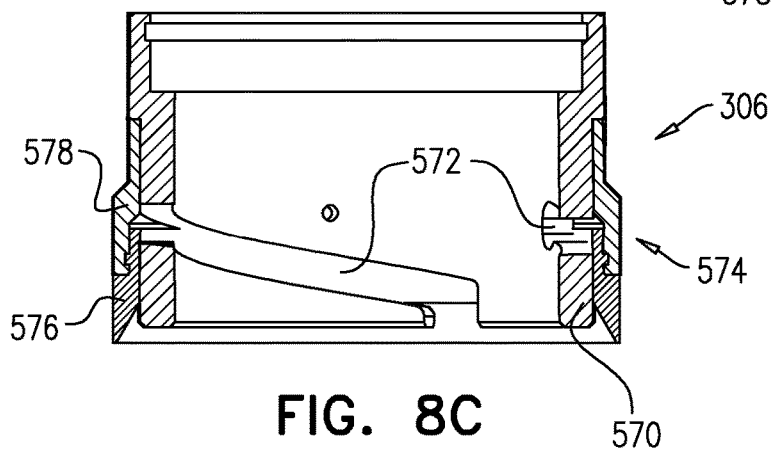
FIG. 8C
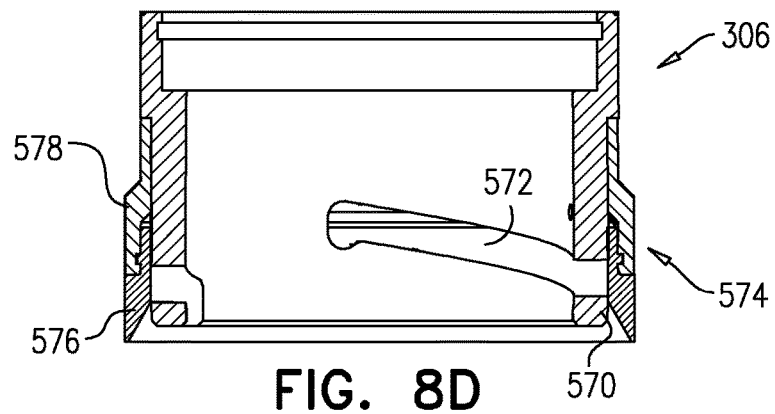
FIG. 8D

ENDOSCOPE ELECTRO-PNEUMATIC ADAPTOR

CROSS-REFERENCE TO RELATED APPLICATIONS

This application is a U.S. National Phase Application under 35 U.S.C. 371 of International Application No. PCT/IL2016/050345, which has an international filing date of Mar. 31, 2016, and which claims the priority benefit of U.S. Provisional Patent Application Ser. No. 62/178,207, filed Apr. 3, 2015, and entitled ADAPTOR FOR USE WITH AN ENDOSCOPE, the description of which is hereby incorporated by reference.

Reference is also made to applicant's Published PCT Patent Applications WO2011/111040; WO/2012/120492; WO/2014/068569 and WO2014/188402, the disclosures of which are hereby incorporated by reference.

FIELD OF THE INVENTION

The present invention relates to endoscope systems generally and more particularly to adaptors useful in endoscope systems.

BACKGROUND OF THE INVENTION

Various types of endoscope systems are known.

SUMMARY OF THE INVENTION

The present invention seeks to provide an improved endoscope system.

There is thus provided in accordance with a preferred embodiment of the present invention an endoscope system including an endoscope including an endoscope electro-pneumatic connection assembly having a leak test port, an endoscope electro-optic subsystem which is connectable to the endoscope via the endoscope electro-pneumatic connection assembly in a manner which precludes access to the leak test port when the endoscope electro-optic subsystem and the endoscope are connected at the electro-pneumatic connection assembly and an electro-pneumatic adaptor, which is connectable to the endoscope at the electro-pneumatic connection assembly and includes an adaptor electro-pneumatic connection assembly, including a leak test port connector for connection to the leak test port of the endoscope, an adaptor electrical port assembly to which the endoscope electro-optic subsystem is connectable and a pneumatic port.

In accordance with a preferred embodiment of the present invention the pneumatic port includes a pneumatic connector assembly. Additionally or alternatively, the electro-pneumatic adaptor is removably connectable to the endoscope at the electro-pneumatic connection assembly. Alternatively or additionally, the leak test port communicates with an interior volume of the endoscope.

Preferably, the electro-pneumatic adaptor includes an electrical connector for connection to an electrical connector of the endoscope, a pneumatic connector portion for connection to the endoscope electro-pneumatic connection assembly and a leak test port connector for connection to the leak test port.

In accordance with a preferred embodiment of the present invention the endoscope is a balloon endoscope and the endoscope system also includes a balloon inflation/deflation subsystem which is connected to the pneumatic port. Additionally, the balloon inflation/deflation subsystem is adapted to provide inflation and deflation of the balloon via the pneumatic port of the adaptor, the leak test port and an interior volume of the endoscope.

In accordance with a preferred embodiment of the present invention the electro-pneumatic adaptor is constructed such that the adaptor electro-pneumatic connection assembly, the adaptor electrical port assembly and the pneumatic port are directed at mutually different angles.

Preferably, the electro-pneumatic adaptor includes a conduit pneumatically connecting the leak test port of the endoscope to the pneumatic port of the adaptor. Additionally or alternatively, the pneumatic port of the adaptor is fixedly connected to at least one of a leak tester and a balloon inflation/deflation subsystem.

In accordance with a preferred embodiment of the present invention the endoscope system also includes a leak tester which is connected to the pneumatic port.

Preferably, the balloon inflation/deflation subsystem is removably connected to the pneumatic port.

There is also provided in accordance with another preferred embodiment of the present invention an electro-pneumatic adaptor for use with an endoscope including an endoscope electro-pneumatic connection assembly having a leak test port, the electro-pneumatic adaptor being connectable to the endoscope at the electro-pneumatic connection assembly and including an adaptor electro-pneumatic connection assembly, including a leak test port connector for connection to the leak test port of the endoscope, an adaptor electrical port assembly and a pneumatic port.

In accordance with a preferred embodiment of the present invention the pneumatic port includes a pneumatic connector assembly. Additionally or alternatively, the electro-pneumatic adaptor is connectable to the endoscope at the electro-pneumatic connection assembly. Preferably, the leak test port communicates with an interior volume of the endoscope.

In accordance with a preferred embodiment of the present invention the adaptor electro-pneumatic connection assembly includes a pneumatic connector portion for connection to the endoscope electro-pneumatic connection assembly and a leak test port connector for connection to the leak test port.

Preferably, the endoscope is a balloon endoscope and the pneumatic port of the electro-pneumatic adaptor is connected to a balloon inflation/deflation subsystem. Additionally, the balloon inflation/deflation subsystem is adapted to provide inflation and deflation of the balloon via the pneumatic port of the adaptor, the leak test port and an interior volume of the endoscope.

In accordance with a preferred embodiment of the present invention the electro-pneumatic adaptor is constructed such that the adaptor electro-pneumatic connection assembly, the adaptor electrical port assembly and the pneumatic port are directed at mutually different angles.

Preferably, the electro-pneumatic adaptor also includes a conduit pneumatically connecting the leak test port of the endoscope to the pneumatic port of the adaptor.

In accordance with a preferred embodiment of the present invention the pneumatic port is fixedly connected to at least one of a leak tester and a balloon inflation/deflation subsystem.

Preferably, the pneumatic port of the electro-pneumatic adaptor is connected to a leak tester. In accordance with a preferred embodiment of the present invention the pneumatic port is removably connected to the balloon inflation/deflation subsystem.

There is further provided in accordance with yet another preferred embodiment of the present invention a method of employing an endoscope system which includes an endoscope including an endoscope electro-pneumatic connection assembly having a leak test port, an endoscope electro-optic subsystem which is connectable to the endoscope via the endoscope electro-pneumatic connection assembly in a manner which precludes access to the leak test port when the endoscope electro-optic subsystem and the endoscope are connected at the electro-pneumatic connection assembly and an electro-pneumatic adaptor, which is connectable to the endoscope at the electro-pneumatic connection assembly and includes an adaptor electro-pneumatic connection assembly, including a leak test port connector for connection to the leak test port of the endoscope, an adaptor electrical port assembly to which the endoscope electro-optic subsystem is connectable and a pneumatic port, the method including connecting the electro-pneumatic adaptor to the endoscope at the electro-pneumatic connection assembly and connecting the endoscope electro-optic subsystem to the adaptor port assembly of the electro-pneumatic adaptor and connecting at least one of a leak tester and a balloon inflation/deflation subsystem to the pneumatic port.

Preferably, at least one of the connecting steps includes removably connecting. Additionally or alternatively, the connecting at least one of the leak tester and the balloon inflation/deflation subsystem to the pneumatic port connects the at least one of the leak tester and the balloon inflation/deflation subsystem to an interior volume of the endoscope.

In accordance with a preferred embodiment of the present invention the method also includes connecting an electrical connector of the adaptor to an electrical connector of the endoscope, connecting a pneumatic connector portion of the adaptor to the endoscope electro-pneumatic connection assembly and connecting the leak test port connector for connection to the leak test port of the endoscope.

Preferably, the endoscope is a balloon endoscope and the method also includes removably connecting the balloon inflation/deflation subsystem to the pneumatic port. Additionally, the balloon inflation/deflation subsystem provides inflation and deflation of the balloon via the pneumatic port of the adaptor, the leak test port and an interior volume of the endoscope.

Preferably, the pneumatic port of the adaptor is fixedly connected to at least one of the leak tester and the balloon inflation/deflation subsystem.

BRIEF DESCRIPTION OF THE DRAWINGS

The present invention will be understood and appreciated more fully from the drawings in which:

FIGS. 3A, 3B and 3C are respectively pictorial assembled, sectional assembled and exploded view illustrations of an electro-pneumatic adaptor forming part of the endoscope systems of FIGS. 1, 2A and 2B, FIG. 3B being a sectional illustration taken along lines IIIB-IIIB in FIG. 3A;

FIGS. 5A, 5B, 5C and 5D are simplified illustrations of a main body portion of the electro-pneumatic adaptor of FIGS. 3A-3C, FIGS. 5A and 5B being pictorial illustrations taken along mutually opposite directions and FIGS. 5C & 5D being respective pictorial and plan view sectional illustrations taken along lines VC-VC in FIG. 5A;

FIGS. 8A, 8B, 8C and 8D are simplified illustrations of a bayonet connection subassembly forming part of the electro-pneumatic adaptor of FIGS. 3A-3C, FIGS. 8A and 8B being pictorial illustrations taken along mutually opposite directions and FIGS. 8C & 8D being sectional illustrations taken along respective lines VIIIC-VIIIC and VIIID-VIIID in FIG. 8A taken along mutually opposite directions;

DETAILED DESCRIPTION OF A PREFERRED EMBODIMENT

Figure 1:
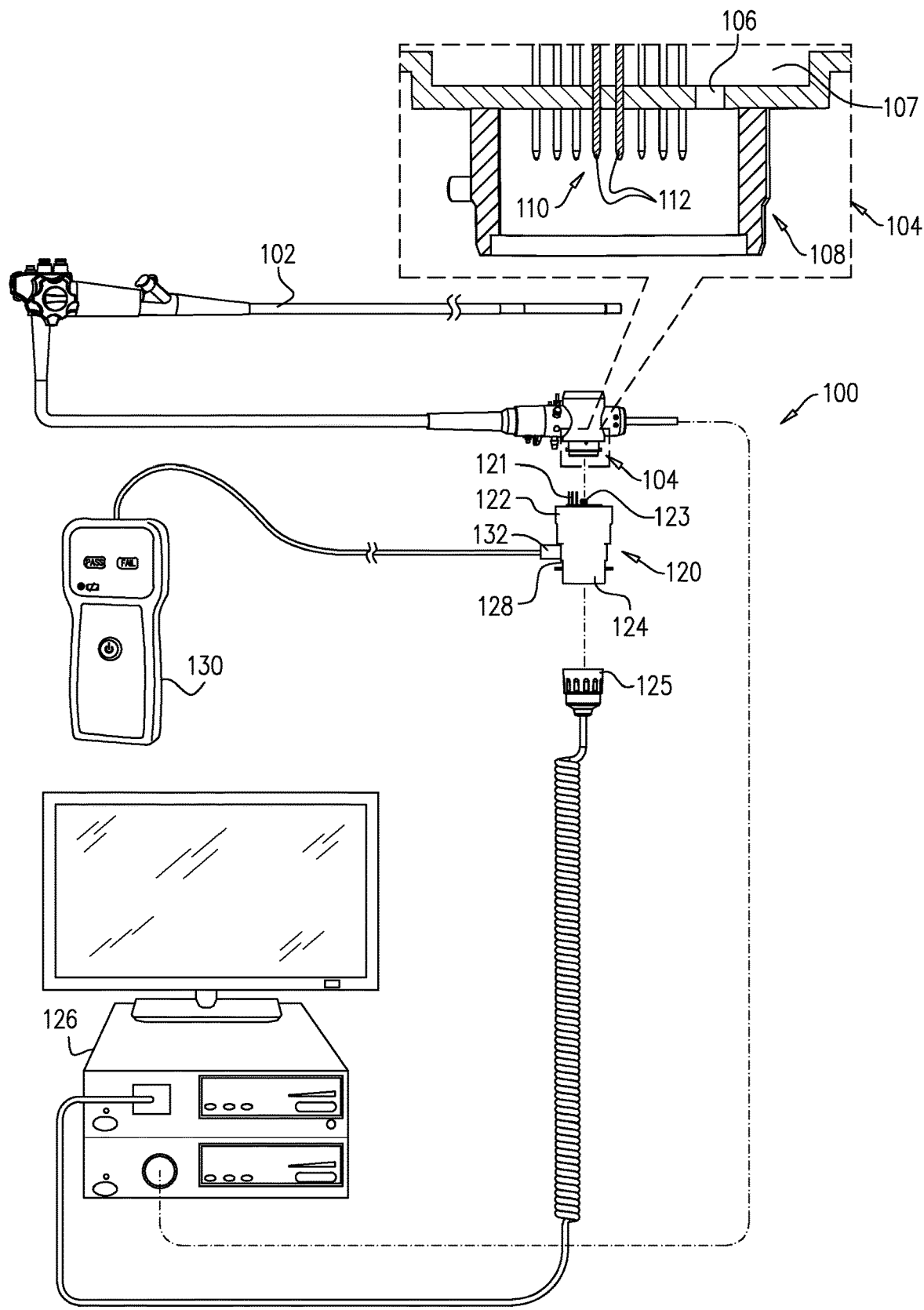
FIG. 1 is a simplified illustration of an endoscope system constructed and operative in accordance with a preferred embodiment of the present invention.

Reference is now made to FIG. 1, which is a simplified illustration of an endoscope system constructed and operative in accordance with a preferred embodiment of the present invention.

As seen in FIG. 1, there is provided an endoscope system 100 comprising an endoscope 102, which may be a suitable conventional endoscope, such as a CF-H180AL colonoscope, commercially available from Olympus Europe GmbH, of Wendenstraße 14-18, 20097, Hamburg, Germany. Endoscope 102 includes an endoscope electro-pneumatic connection assembly 104, including a leak test port 106 communicating with an interior volume 107 of endoscope 102, and includes a pneumatic connector portion 108 and an electrical connector 110 including a plurality of male pins 112.

In accordance with a preferred embodiment of the present invention there is provided an electro-pneumatic adaptor 120, which is removably connectable to endoscope 102 at the endoscope electro-pneumatic connection assembly 104 and includes an electrical connector 121, comprising a plurality of pins, for connection to electrical connector 110 of endoscope 102, a pneumatic connector portion 122 for connection to the pneumatic connector portion 108 of the endoscope electro-pneumatic connection assembly 104 and a leak test port connector 123 which engages the leak test port 106. The electro-pneumatic adaptor 120 also includes an adaptor electrical port connector 124 to which a connector 125 of an endoscope electro-optic subsystem 126 is connectable and a pneumatic connector assembly 128 for connection to a leak testing subsystem 130 via a leak testing subsystem connector 132. Leak testing subsystem connector 132 may be any suitable pneumatic connector, and preferably is similar to a conventional connector, forming part of conventional leak tester such as model SHA-P5, commercially available from Pentax Europe GmbH, of 104 Julius-Vosseler St., 22527 Hamburg, Germany.

In accordance with a preferred embodiment of the present invention the leak testing subsystem 130 communicates with the interior volume 107 of the endoscope 102 via leak test port 106.

Endoscope electro-optic subsystem 126 is a conventional endoscope electro-optical subsystem such as a CV-180 video processor, commercially available from Olympus Europe GmbH, of Wendenstraße 14-18, 20097, Hamburg, Germany.

It is appreciated that during conventional clinical use of endoscope 102 in performing an endoscopy examination, as known in the art, the endoscope 102 is connected directly to endoscope electro-optic subsystem 126, by connecting the connector 125 to endoscope electro-pneumatic connection assembly 104, thereby precluding access to leak test port 106 during the endoscopy procedure. It is further appreciated that preclusion of pneumatic access to leak test port 106 and thus to the interior volume 107 of endoscope 102, when said endoscope electro-optic subsystem 126 and said endoscope 102 are connected at said electro-pneumatic connection assembly 104, prevents leak testing of endoscope 102 during the endoscopy examination.

It is a particular feature of the present invention that electro-pneumatic adaptor 120 enables simultaneous electrical connection of endoscope 102 and endoscope electro-optic subsystem 126, and pneumatic communication between an external pneumatic device such as leak tester 130 and the leak test port 106 of endoscope 102, thereby enabling leak testing of endoscope 102 during an endoscopy examination.

Figure 2A:
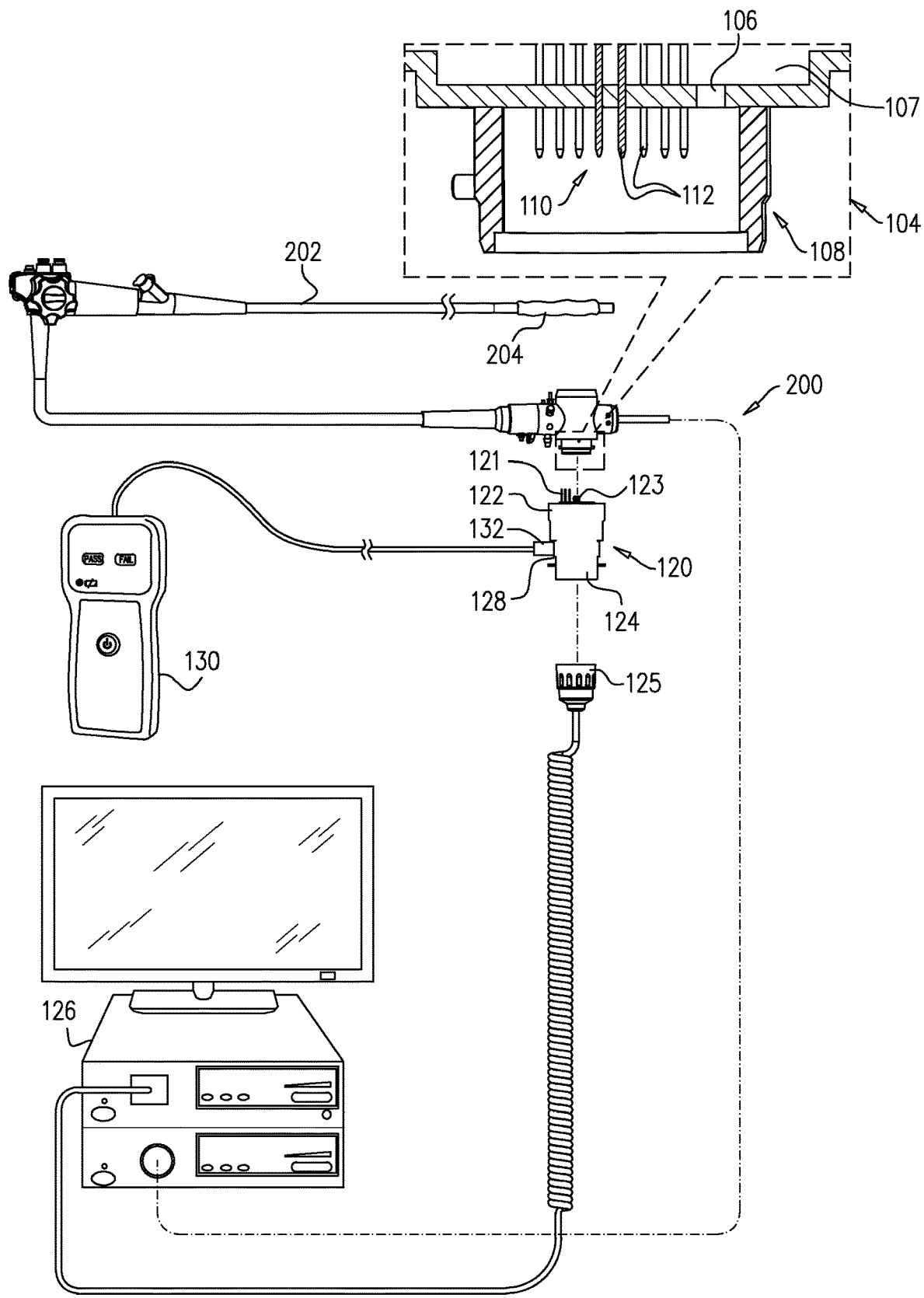
FIGS. 2A and 2B are simplified illustrations of a balloon endoscope system constructed and operative in accordance with another preferred embodiment of the present invention showing respective connections to a leak testing subsystem and to a balloon inflation/deflation subsystem.

Reference is now made to FIG. 2A, which is a simplified illustration of a balloon endoscope system constructed and operative in accordance with a preferred embodiment of the present invention.

As seen in FIG. 2A, there is provided a balloon endoscope system 200 comprising a balloon endoscope 202, which may be a suitable conventional balloon endoscope, such as a G-EYE™ H180AL colonoscope, commercially available from Smart Medical Systems, of 10 Hayetsira street, 4366356, Ra'anana, Israel. Aside from including a balloon 204, balloon endoscope 202 may be identical in all relevant respects to endoscope 102 (FIG. 1) and balloon endoscope system 200 may be identical in all relevant respects to endoscope system 100, identical elements being designated by identical reference numerals. Adaptor 120 is connected to a leak testing subsystem 130 via connector 132.

Figure 2B:
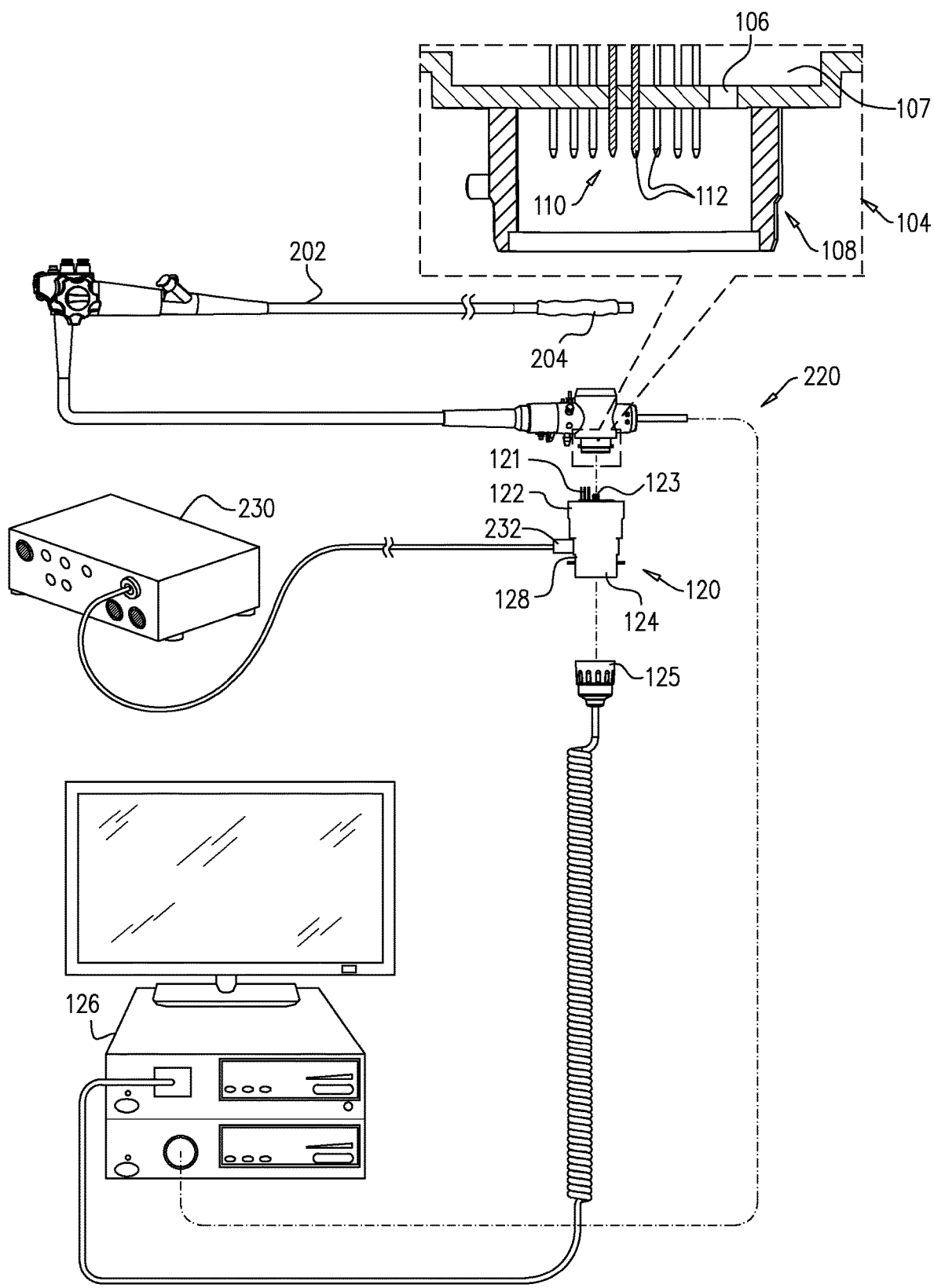

It is a particular feature of the present invention that electro-pneumatic adaptor 120 enables simultaneous electrical connection of balloon endoscope 202 and endoscope electro-optic subsystem 126, and pneumatic communication between an external pneumatic device such as leak tester 130 and the leak test port 106 of balloon endoscope 202, thereby enabling leak testing of balloon endoscope 202 during an endoscopy examination. Reference is now made to FIG. 2B, which is a simplified illustration of a balloon endoscope system 220, which is identical to the balloon endoscope system 200 of FIG. 2A but is connected to an inflation/deflation subsystem 230, via a connector 232, which may be identical to connector 132, instead of to a leak testing subsystem 130 as in the embodiment of FIG. 2A. In accordance with a preferred embodiment of the present invention the inflation/deflation subsystem communicates with the interior volume of the endoscope via leak test port 106 and provides inflation and deflation of the balloon 204 via the interior volume 107.

It is appreciated that had balloon endoscope 202 been connected directly to endoscope electro-optic subsystem 126 while performing an endoscopy examination, by connecting the connector 125 to endoscope electro-pneumatic connection assembly 104 as commonly known in the art, this would have precluded access to leak test port 106 and consequently would have precluded inflation and deflation of balloon 204 through interior volume 107 by inflation/deflation subsystem 230 during the endoscopy examination.

It is a particular feature of the present invention that electro-pneumatic adaptor 120 enables simultaneous electrical connection of balloon endoscope 202 and endoscope electro-optic subsystem 126, and pneumatic communication between an external pneumatic device such as inflation/deflation subsystem 230 and the interior of balloon endoscope 202, via the leak test port 106, thereby enabling inflation and deflation of balloon 204 of balloon endoscope 202 during an endoscopy examination.

Figure 3C:
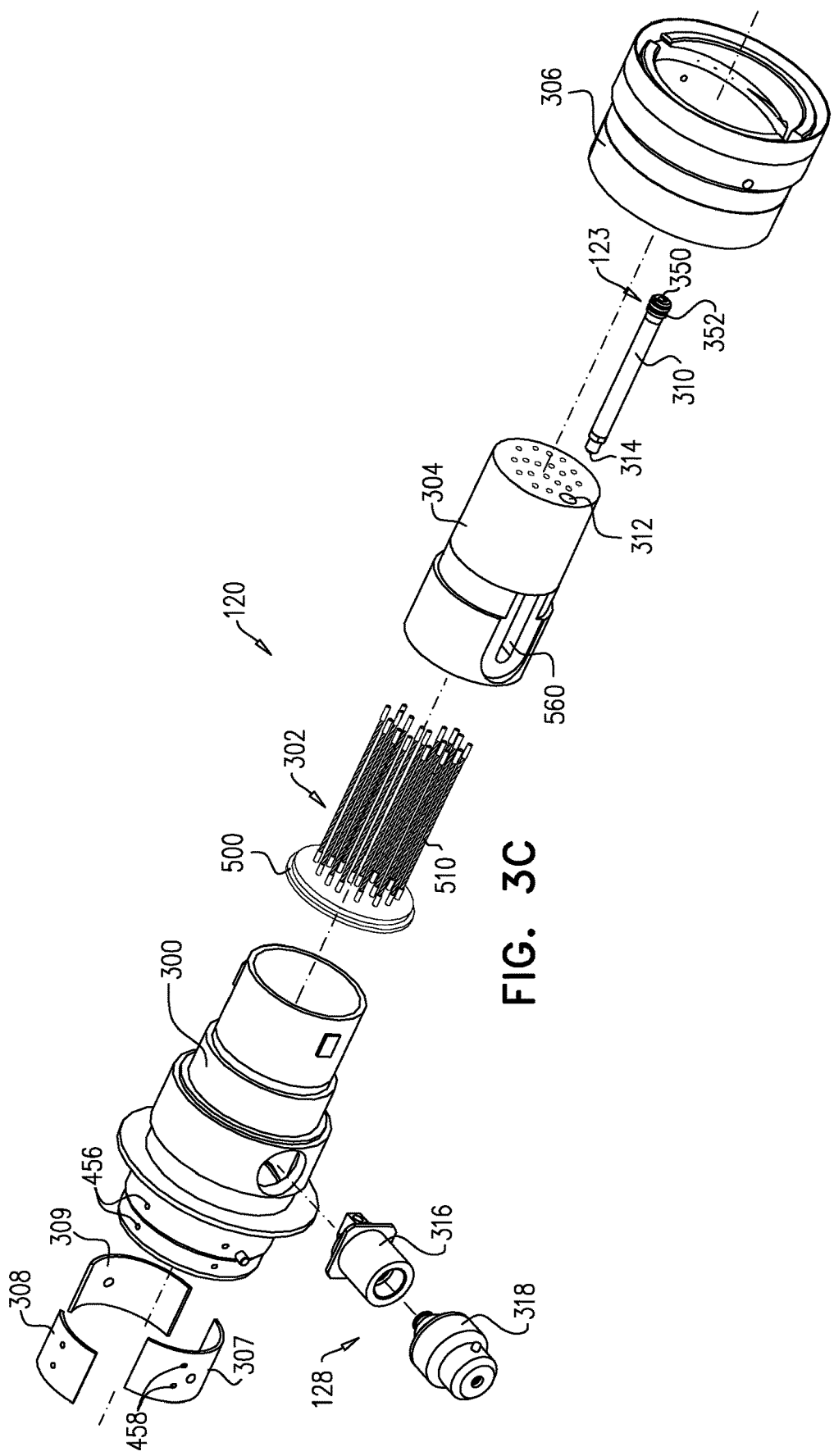

Reference is now made to FIGS. 3A, 3B and 3C, which are respectively pictorial assembled, sectional assembled and exploded view illustrations of electro-pneumatic adaptor 120, forming part of the endoscope systems of FIGS. 1 and 2.

As seen in FIGS. 3A, 3B and 3C, the electro-pneumatic adaptor 120 comprises a main body portion 300, an adaptor electrical connector assembly 302, an electrical connector support block 304 and a bayonet connector assembly 306, for connection to endoscope electro-pneumatic connection assembly 104 (FIG. 1). Retaining shims 307, 308 and 309 are employed to retain adaptor electrical connector assembly 302 in main body portion 300.

A pneumatic conduit 310 extends through a channel 312 formed in electrical connector support block 304 and is coupled at one end 314 thereof to pneumatic connector assembly 128 (FIG. 1). It is seen clearly in FIGS. 3B and 3C that pneumatic connector assembly 128 includes first and second pneumatic connector elements 316 and 318.

Figure 4A:
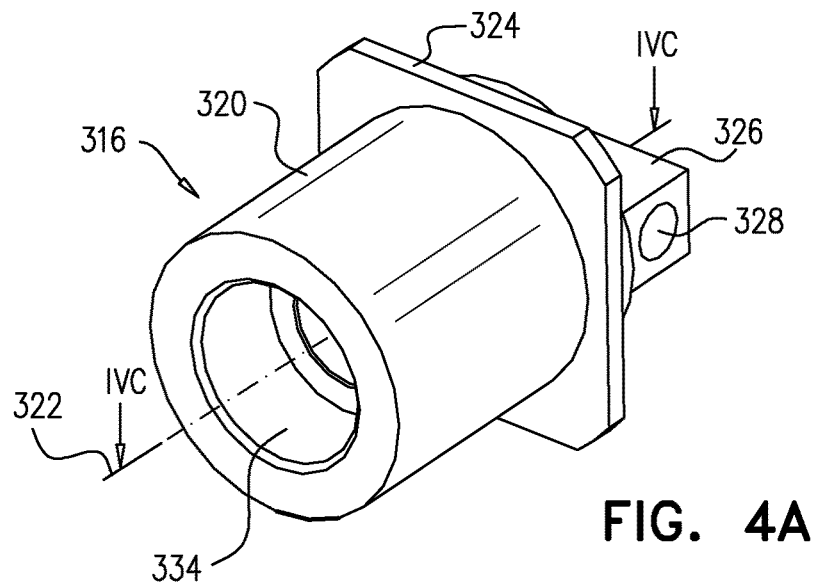
FIGS. 4A, 4B and 4C are simplified illustrations of a first pneumatic connector element, forming part of the electro-pneumatic adaptor of FIGS. 3A-3C, FIG. 4C being a sectional illustration taken along lines IVC-IVC in FIG. 4A.
Figure 4B:
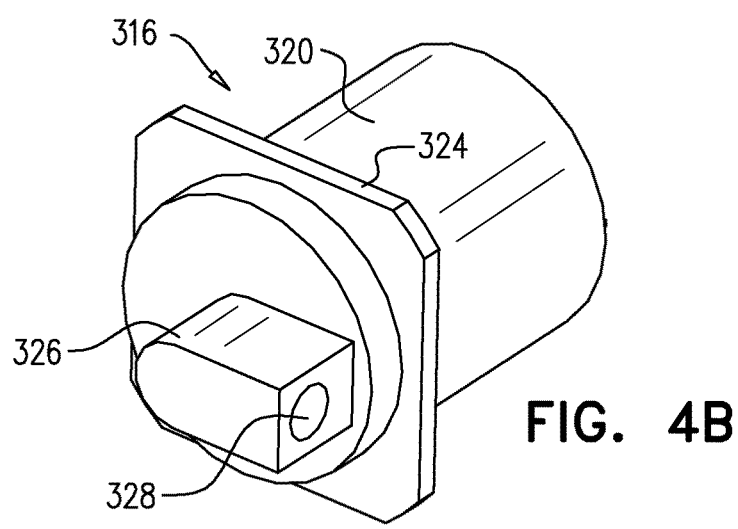
Figure 4C:
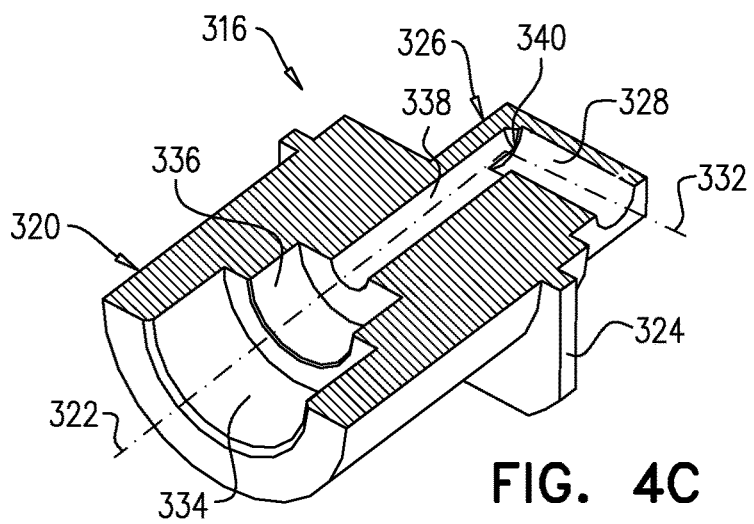
Figures 5C, 5D:
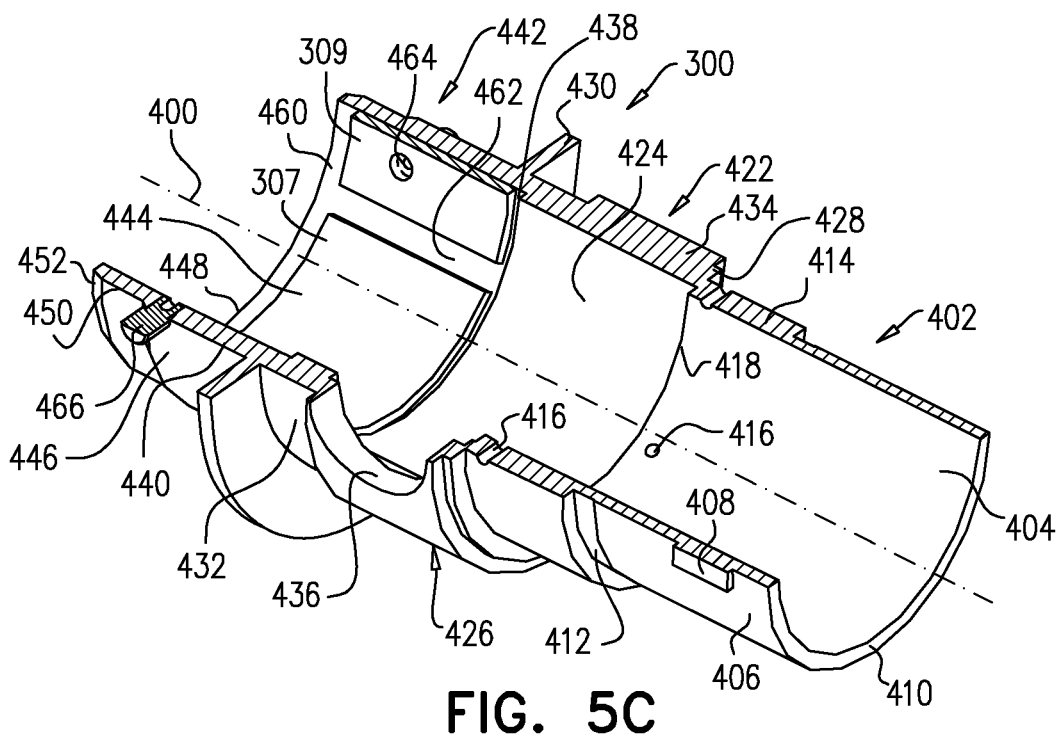

First pneumatic connector element 316 is illustrated in FIGS. 4A-4C, to which reference is now made, and includes a generally circular cylindrical portion 320, having a longitudinal axis 322, which is integrally formed with a generally square flange portion 324, which extends in a plane generally perpendicular to longitudinal axis 322. An inner portion 326 extends inwardly from flange portion 324 and includes a bore 328 which extends along an axis 332, which intersects and is perpendicular to longitudinal axis 322.

Generally circular cylindrical portion 320 includes an outer bore portion 334, inwardly of which is defined an inner bore portion 336, both of which extend along longitudinal axis 322. Inner bore portion 336 terminates in a bore 338, which also extends along longitudinal axis 322 and intersects with and joins bore 328 at a 90 degree junction 340.

Second pneumatic connector element 318 may be a conventional pneumatic connector, such as EOG valve assembly model number D201-V2330-1, commercially available from Pentax Europe GmbH, of 104 Julius-Vosseler St., 22527 Hamburg, Germany.

Pneumatic conduit 310 is arranged to be coupled at an end 350 thereof, which constitutes leak test port connector 123 (FIG. 1) and is preferably equipped with an O-ring 352, to leak test port 106 (FIG. 1).

Main body portion 300 is illustrated in detail in FIGS. 5A-5D, to which reference is now made. As seen in FIGS. 5A-5D, main body portion 300 is a generally circularly symmetric integrally formed element arranged about a longitudinal axis 400 which includes a first generally circular cylindrical portion 402 having a generally circular cylindrical inner surface 404 and a generally circular cylindrical outer surface 406. Formed on generally circular cylindrical outer surface 406 are a plurality of mutually spaced generally rectangular radial protrusions 408, whose azimuthal distribution is shown in a sectional view portion of FIG. 5A.

Generally circular cylindrical outer surface 406 extends from an edge 410 to a shallow circumferential undercut 412. Adjacent undercut 412 is a circumferential protrusion 414 having formed therein a plurality of mutually spaced, radially extending apertures 416. Generally circular cylindrical inner surface 404 extends from edge 410 to a shoulder 418.

Axially adjacent first generally circular cylindrical portion 402 is a second generally circular cylindrical portion 422, having a generally circular cylindrical inner surface 424 and a generally circular cylindrical outer surface 426.

Generally circular cylindrical outer surface 426 extends from a shoulder 428 axially to a generally circular flange 430, axially adjacent to which is a relative undercut portion 432. Generally circular cylindrical outer surface 426 includes a circumferential protrusion 434 having formed therein a side aperture 436. Generally circular cylindrical inner surface 424 extends from shoulder 418 to a shoulder 438 and includes a side recess 440 surrounding side aperture 436.

Axially adjacent second generally circular cylindrical portion 422 is a third generally circular cylindrical portion 442, having a generally circular cylindrical inner surface 444 and a generally circular cylindrical outer surface 446.

Generally circular cylindrical outer surface 446 extends from flange 434 to an edge 448 and includes a forward undercut portion 450 and a chamfered portion 452 adjacent edge 448. Generally circular cylindrical inner surface 444 extends from shoulder 438 to edge 448. Disposed within and adjacent generally circular cylindrical inner surface 444 are mutually azimuthally spaced retaining shims 307, 308 and 309 (FIG. 3C), which are employed to retain adaptor electrical connector assembly 302 in main body portion 300. Shims 307, 308 and 309 are attached to main body portion, preferably by screws 454 which extend via apertures 456 formed in main body portion 300 and into correspondingly positioned threaded recesses 458 formed on outer surfaces of shims 307, 308 and 309.

Shims 307, 308 and 309 are attached to main body portion 300 only after insertion of adaptor electrical connector assembly 302 into main body portion 300 and are located so as to define therebetween a circumferential edge recess 460 and a plurality of axial recesses 462 which extend from circumferential edge recess 460 to shoulder 438.

A plurality of radially extending apertures 464 are formed in third generally circular cylindrical portion 442 and retain therein radially outwardly extending pins 466.

Figure 6:
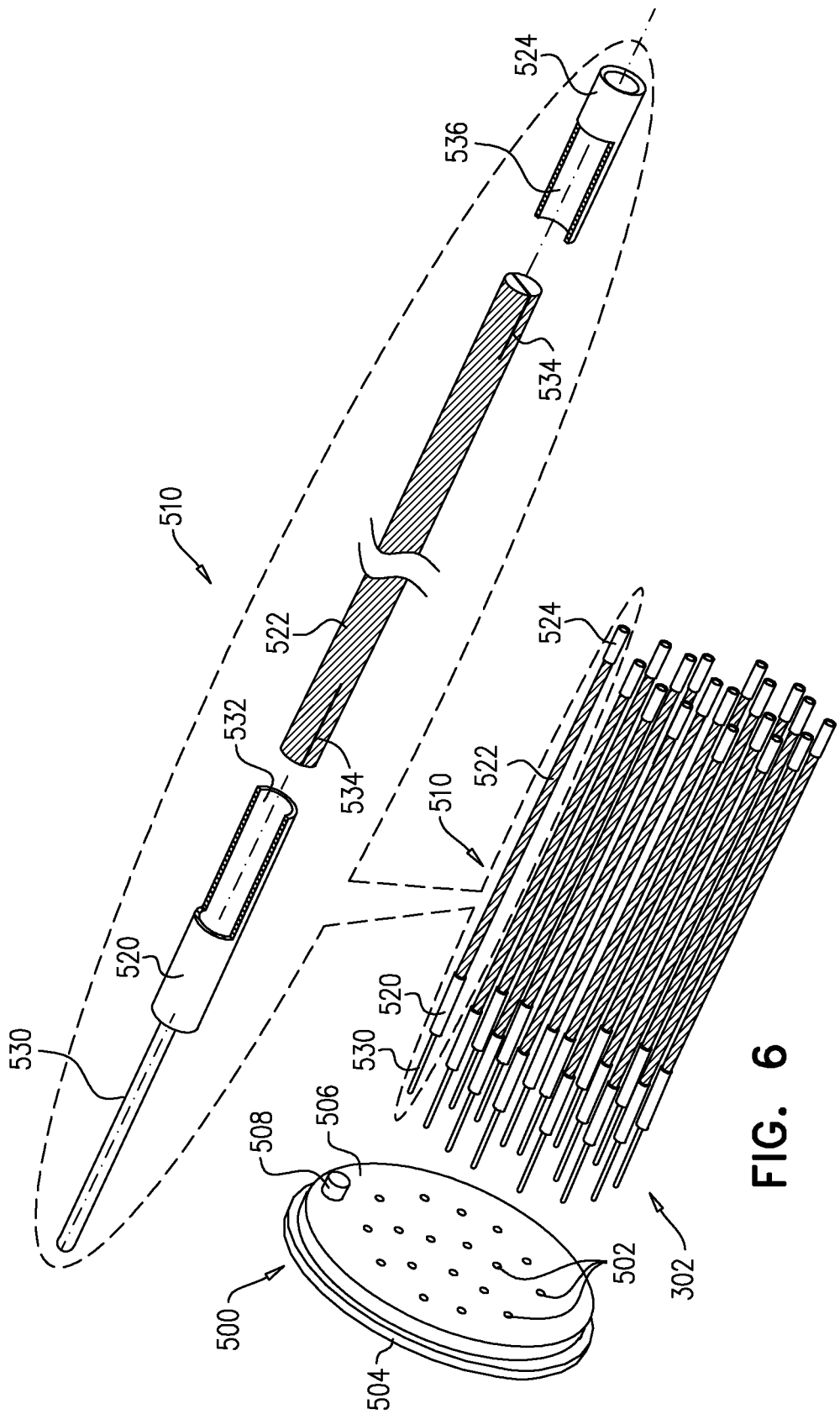
FIG. 6 is a simplified illustration of an adaptor electrical connector assembly forming part of the electro-pneumatic adaptor of FIGS. 3A-3C.

Adaptor electrical connector assembly 302 is illustrated in FIG. 6, to which reference is now made, and includes a base element 500 having a plurality of mutually spaced pin apertures 502 extending therethrough from a first generally planar surface 504 to a second planar surface 506. Second planar surface 506 is provided with an azimuthal orientation protrusion 508.

A plurality of electrical contact pin assemblies 510 are mounted onto base element 500, each at a pin mounting aperture 502, extending through base element 500. Each of electrical contact pin assemblies 510 preferably includes a male pin element 520 which is configured to be seated in and extend through base element 500, a generally circularly cylindrical intermediate pin shaft 522, and a female pin element 524.

Male pin element 520 is preferably an integrally formed element and includes an axial pin portion 530 and a socket 532 for retainably receiving a first end of intermediate pin shaft 522. Generally circularly cylindrical intermediate pin shaft 522 is preferably an elongate shaft, preferably having end slits 534 formed therein to provide resiliency. Female pin element 524 preferably is an integrally formed hollow cylindrical element, one end of which defines a socket 536 for retainably receiving a second end of intermediate pin shaft 522.

Figure 7A:
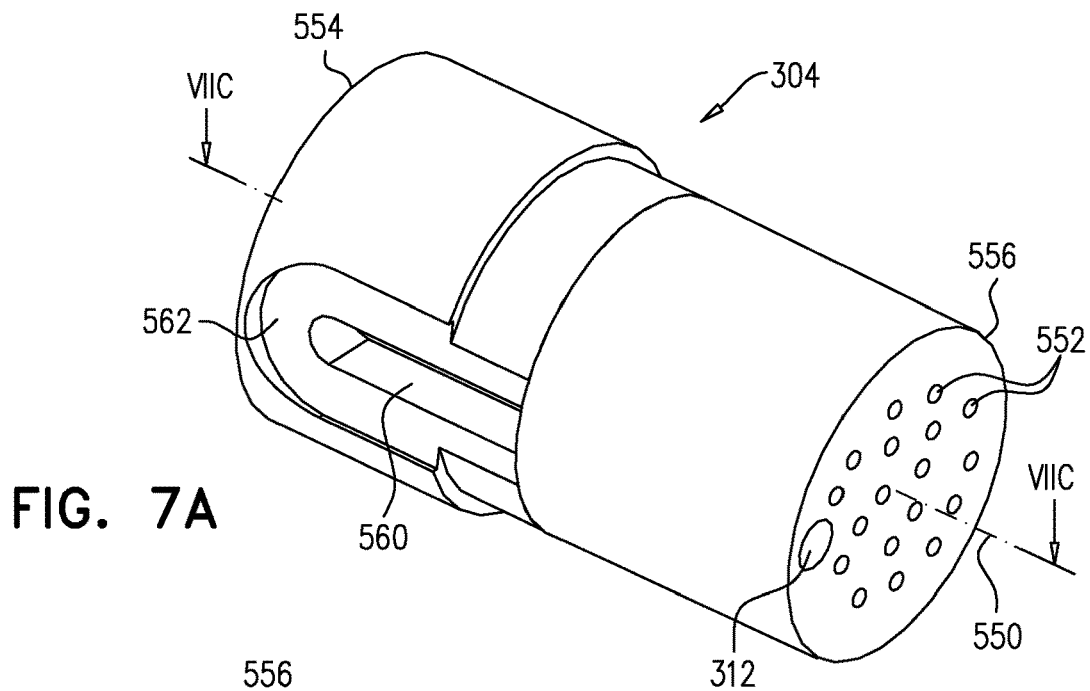
FIGS. 7A, 7B and 7C are simplified illustrations of an electrical connector support block, forming part of the electro-pneumatic adaptor of FIGS. 3A-3C, FIG. 7C being a sectional illustration taken along lines VIIC-VIIC in FIG. 7A.
Figure 7B:
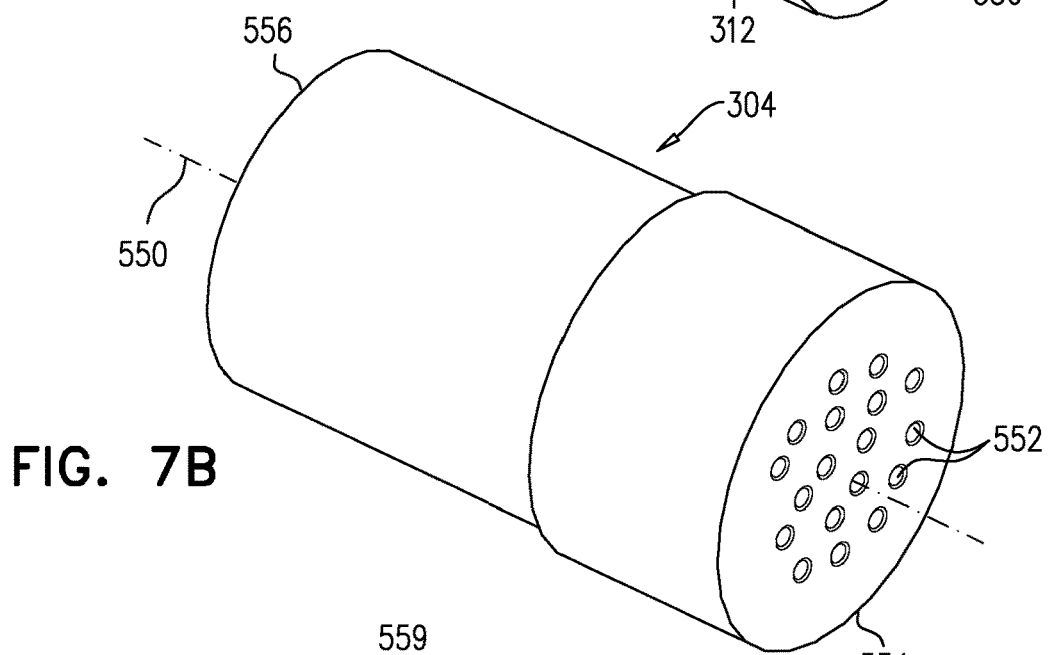
Figure 7C:
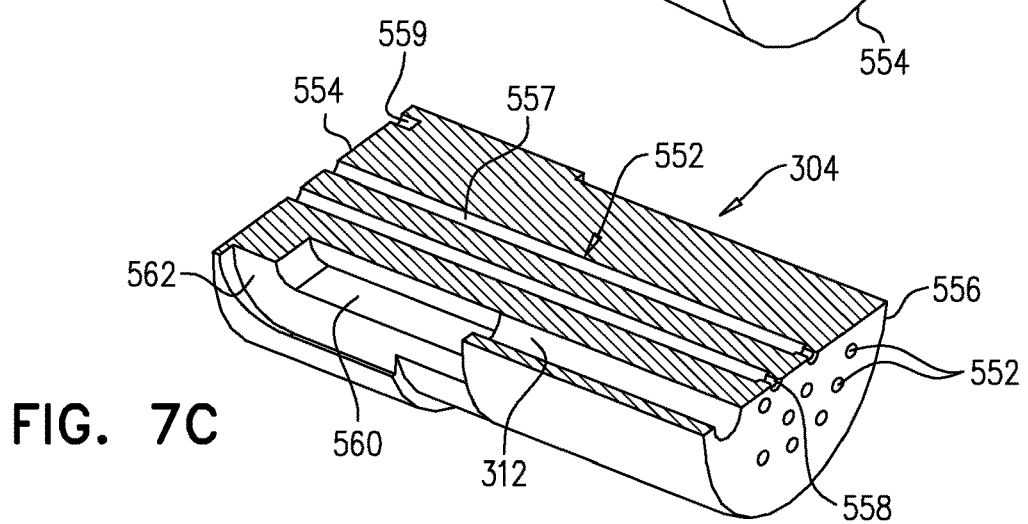
Figure 9A:
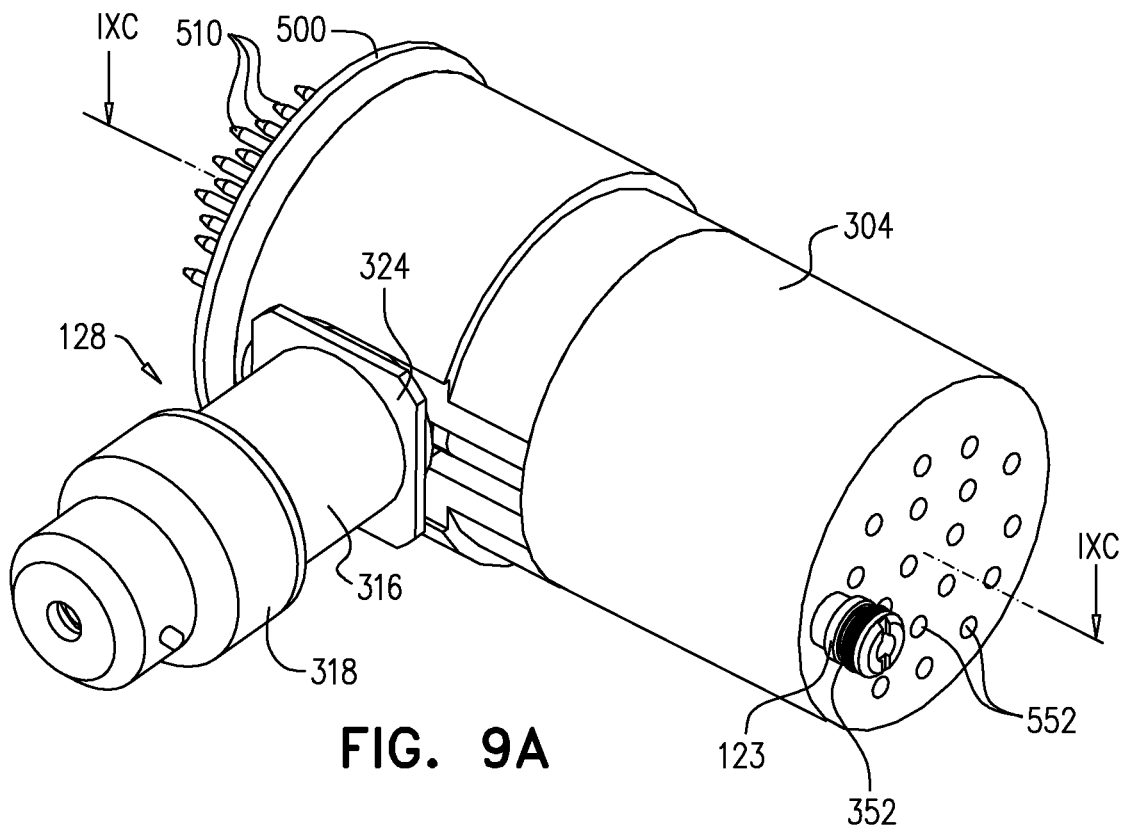
FIGS. 9A, 9B, 9C and 9D are simplified illustrations of the electro-pneumatic adaptor of FIGS. 3A-3C without the main body portion and without the bayonet connection subassembly, FIGS. 9A and 9B being pictorial illustrations taken along mutually opposite directions and FIGS. 9C & 9D being respective pictorial and plan view sectional illustrations taken along lines IXC-IXC in FIG. 9A.
Figure 9B:
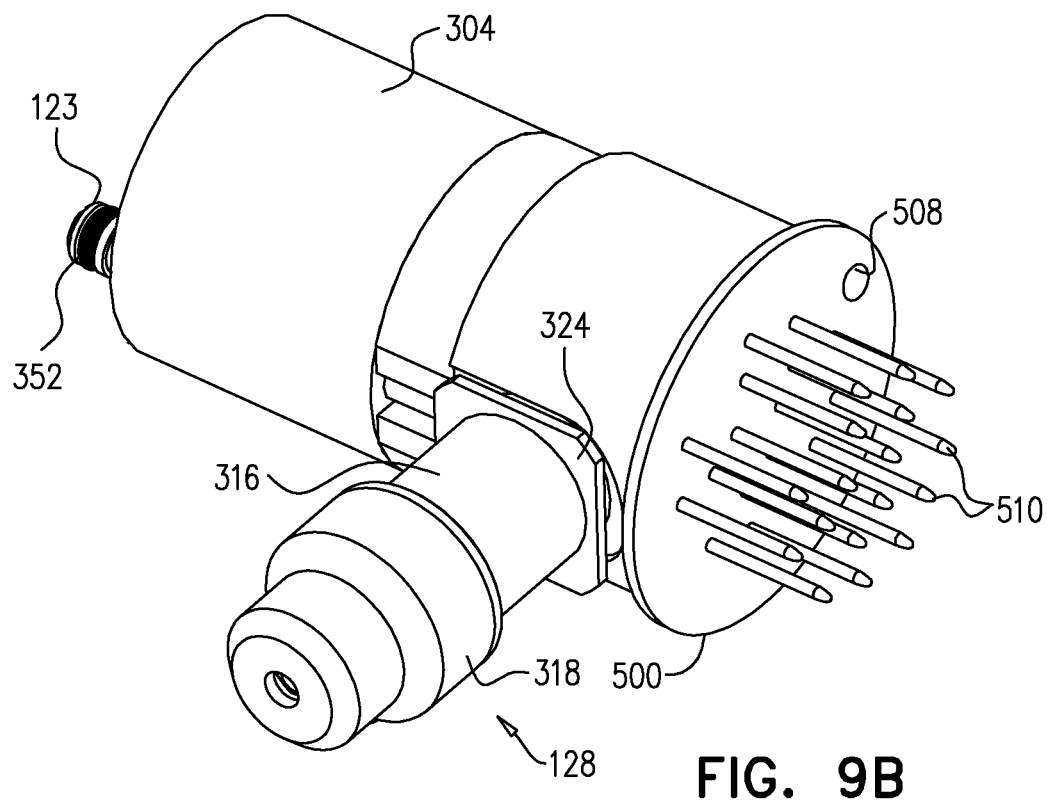
Figure 9C:
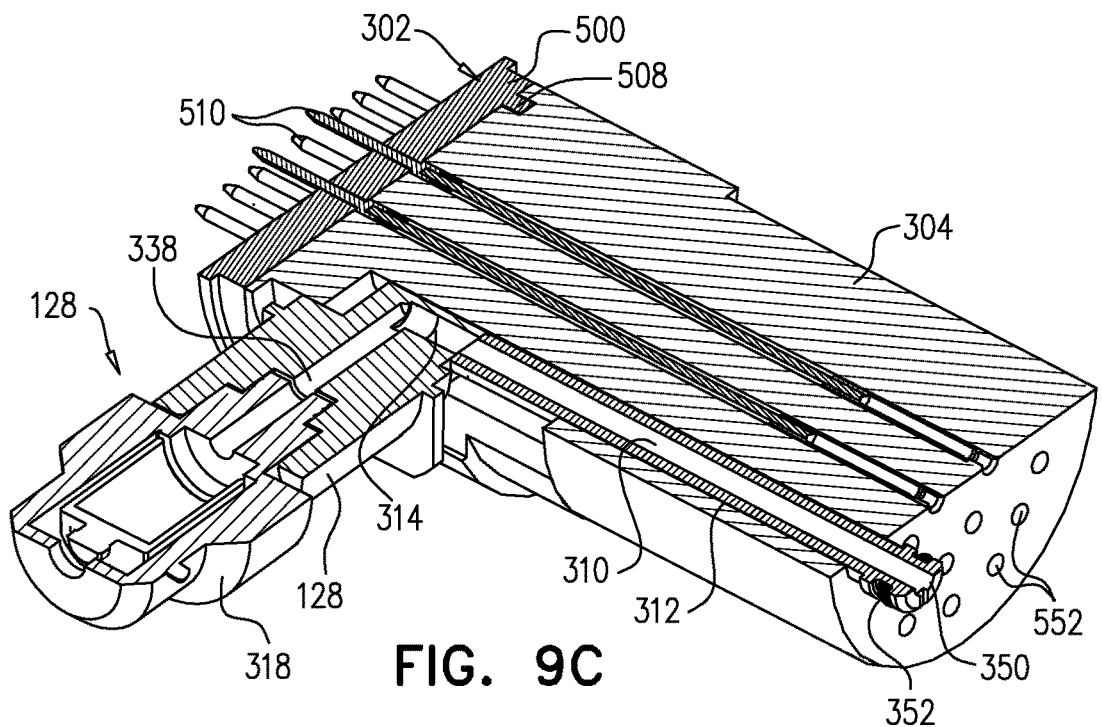
Figure 9D:
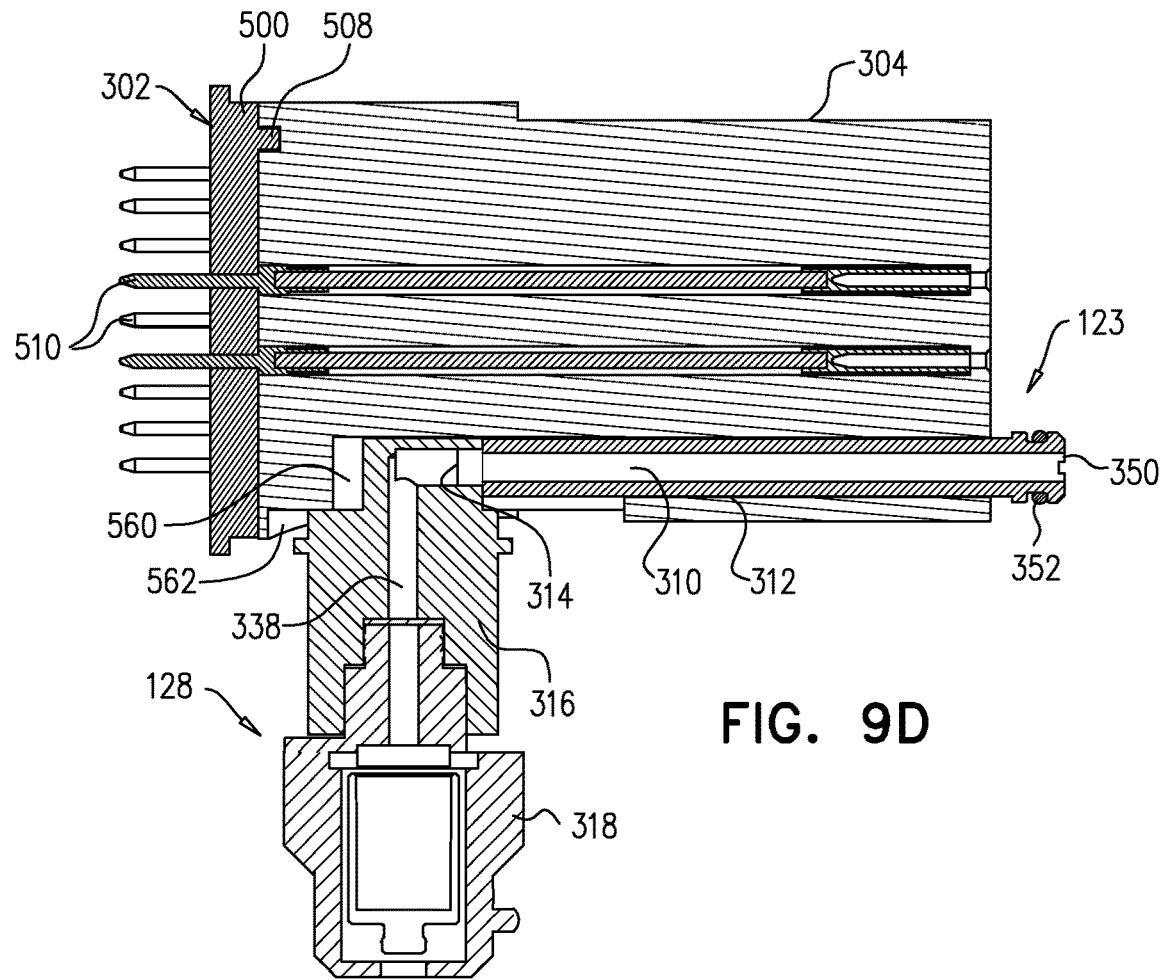

Electrical connector support block 304 is illustrated in FIGS. 7A-7C, to which reference is now made. As seen in FIGS. 7A-7C, electrical connector support block 304 is preferably an integrally formed, generally cylindrical element extending along an axis 550 and is preferably formed of a dielectric material such as DELRIN, ABS, or OKOLON.

Electrical connector support block 304 is preferably formed with a plurality of throughgoing generally circular cylindrical bores 552 which extend from a first end 554 of block 304 to a second end 556 of block 304. Bores 552 having a generally uniform cross-sectional radius along most of their extent 557 from first end 554 and have a short extent 558 adjacent second end 556 which has a lesser cross sectional radius. Each electrical contact pin assembly 510 is retained in an extent 557 of a bore 552. A recess 559 is formed at first end 554 of block 304 to accommodate azimuthal orientation protrusion 508 (FIG. 6).

As seen particularly in FIG. 7C, channel 312 terminates in a recess 560, which lies within an external recess 562, both of which accommodate an end of first pneumatic connector element 316.

Bayonet connector assembly 306 is illustrated in FIGS. 8A-8D, to which reference is now made. The overall construction and operation of bayonet connector assembly 306 is similar to that in Olympus MAJ-1430 Pigtail, commercially available from Olympus Europe GmbH, of Wendenstraße 14-18, 20097, Hamburg, Germany. Briefly stated, the bayonet connector assembly 306 includes a main cylindrical portion 570 having a pair of angled circumferential bayonet pin receiving slits 572 formed therein. A locking ring assembly 574, including a forward portion 576 and a rearward portion 578, cooperates with main cylindrical portion 570 in a conventional manner and is preferably spring loaded in a conventional manner. Details of the conventional bayonet connector assembly 306 are not shown or described in detail.

FIGS. 9A-9D illustrate the assembly of elements 302, 304, 310, 316 and 318 as described in detail hereinabove.

Figure 10A:
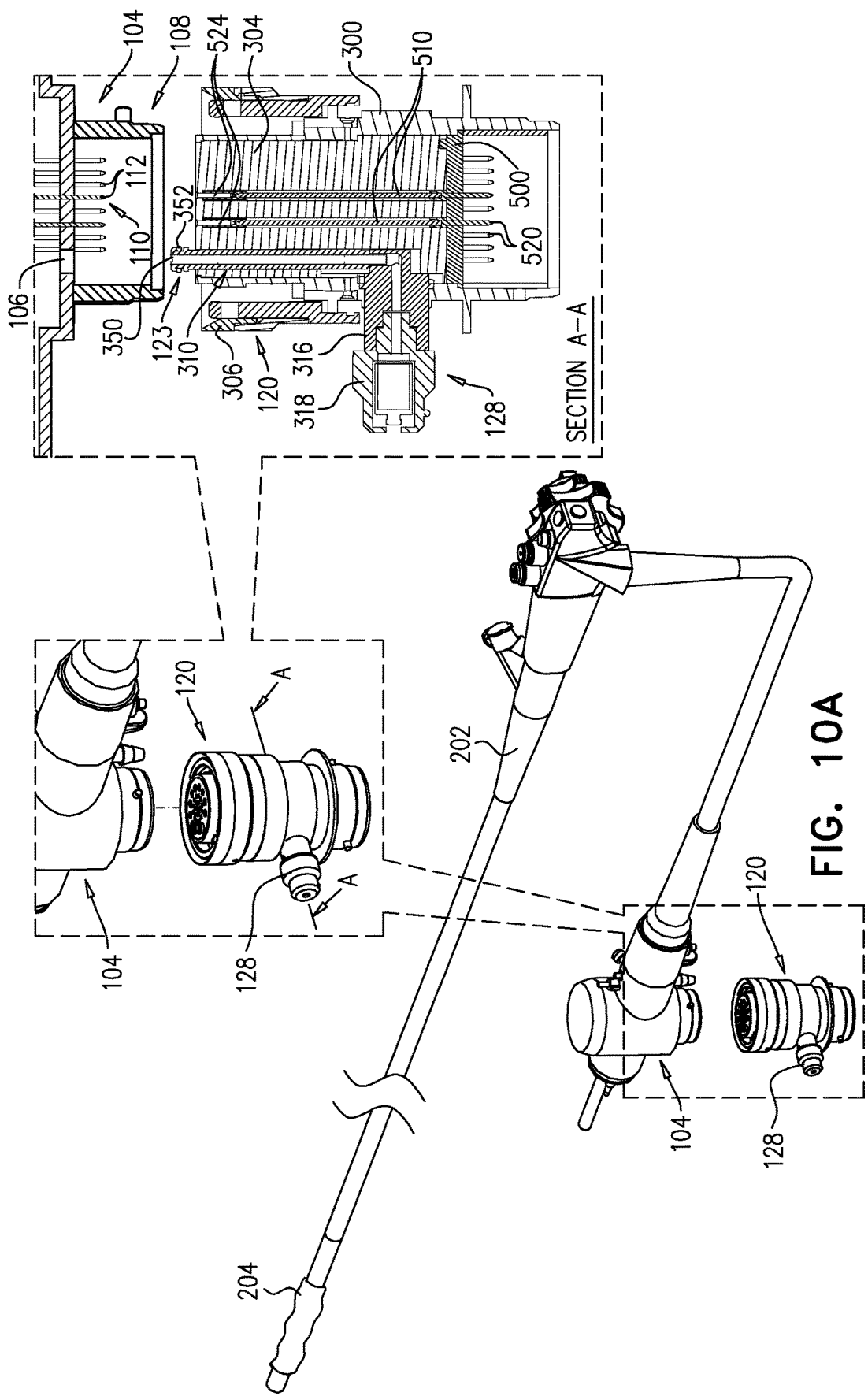
FIGS. 10A and 10B are simplified illustrations showing two operative orientations of the electro-pneumatic adaptor of FIGS. 3A-3C relative to an endoscope forming part of the balloon endoscope system of FIGS. 2A and 2B.
Figure 10B:
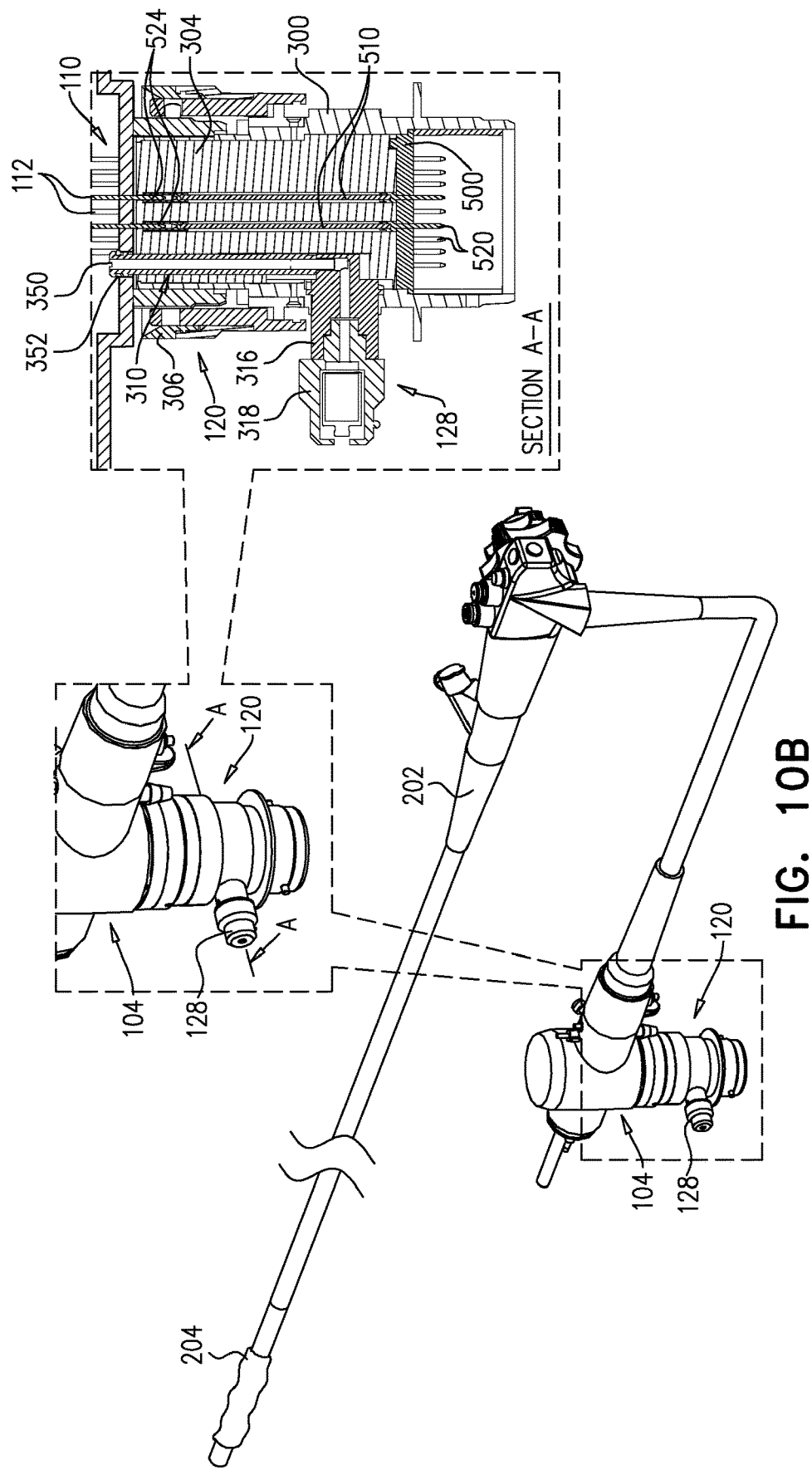

Reference is now made to FIGS. 10A and 10B, which are simplified illustrations showing two operative orientations of the electro-pneumatic adaptor of FIGS. 3A-3C relative to an endoscope forming part of the balloon endoscope system of FIGS. 2A and 2B. In FIG. 10A, it is seen that the electro-pneumatic adaptor 120 is entirely disconnected from the balloon endoscope 202.

In FIG. 10B, it is seen that the electro-pneumatic adaptor 120 is connected to the balloon endoscope 202, such that the pneumatic conduit 310 is sealingly coupled at an end 350 thereof, which constitutes leak test port connector 123 (FIG. 1) and is equipped with an O-ring 352, to leak test port 106 (FIG. 1) of balloon endoscope 202. It is also seen that male pins 112 of electrical connector 110 of balloon endoscope 202 are each inserted into a corresponding female pin element 524 of electrical contact pin assembly 510 of adaptor 120.

Figure 11A:
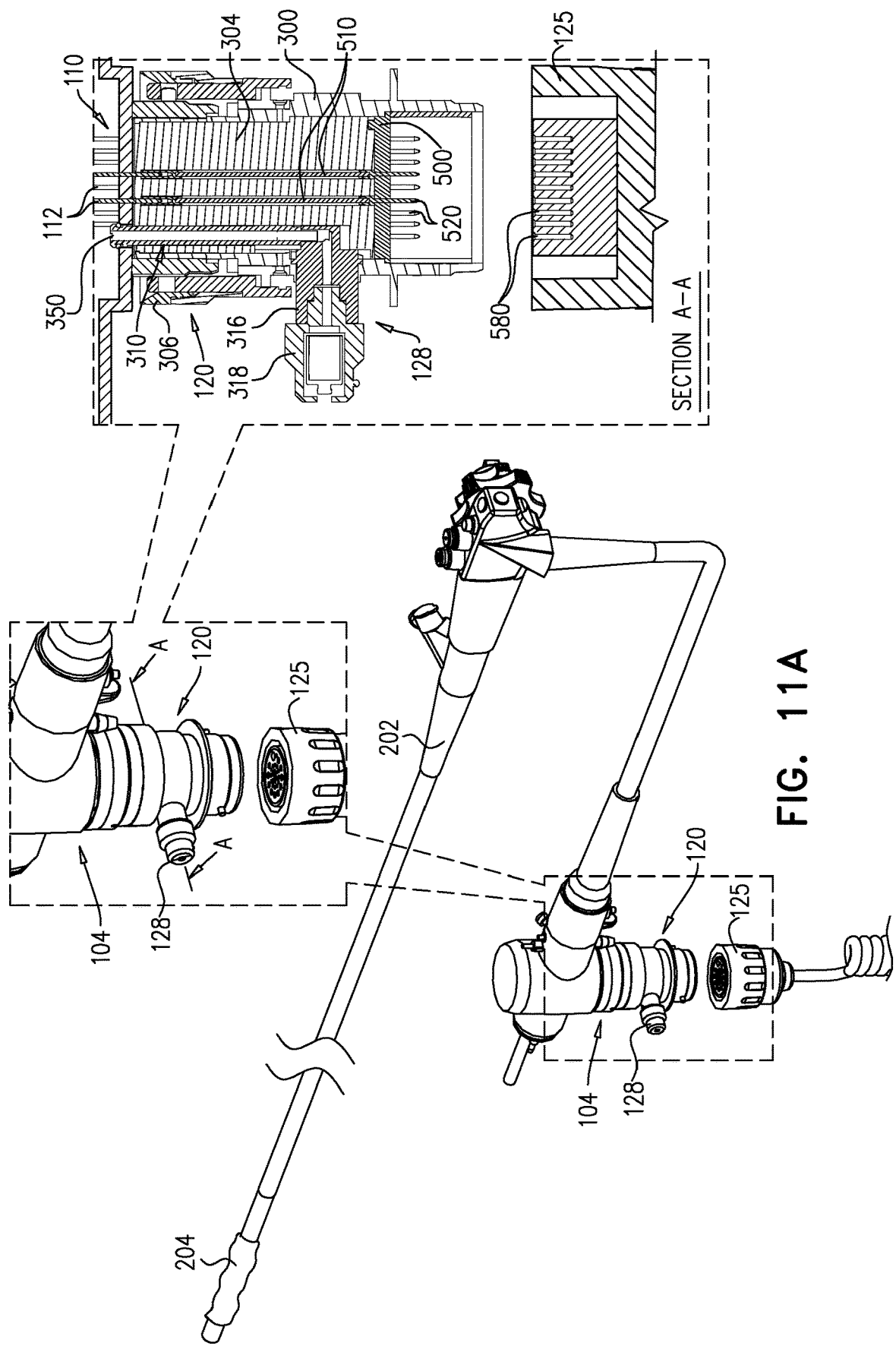
FIGS. 11A and 11B are simplified illustrations showing two operative orientations of the electro-pneumatic adaptor of FIGS. 3A-3C when connected to an electro-optic subsystem forming part of the balloon endoscope system of FIGS. 2A and 2B.
Figure 11B:
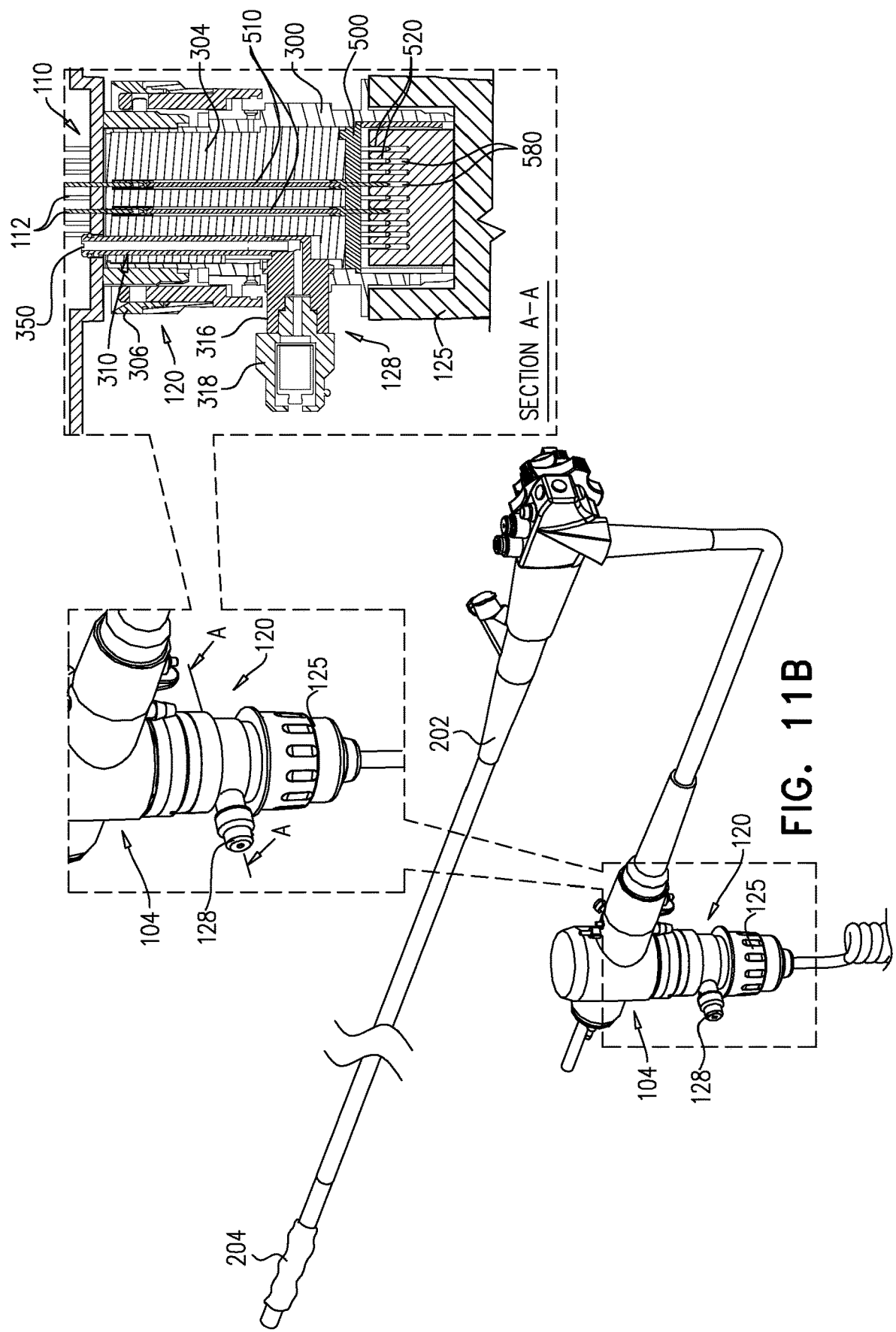

Reference is now made to FIGS. 11A and 11B, which are simplified illustrations showing two operative orientations of the electro-pneumatic adaptor of FIGS. 3A-3C relative to an electro-optic subsystem forming part of the balloon endoscope system of FIGS. 2A and 2B. In FIG. 11A, it is seen that the electro-pneumatic adaptor 120 is connected to the balloon endoscope 202 but is entirely disconnected from the electro-optic subsystem 126 and connector 125 (FIG. 1).

In FIG. 11B, it is seen that axial pin portions 530 of electrical contact pin assemblies 510 of adaptor 120 are each inserted into a corresponding pin socket in connector 125. It is also seen that male pins 520 of electrical contact pin assembly 510 of adaptor 120 are each inserted into a corresponding female pin socket 580 of connector 125.

Figure 12A:
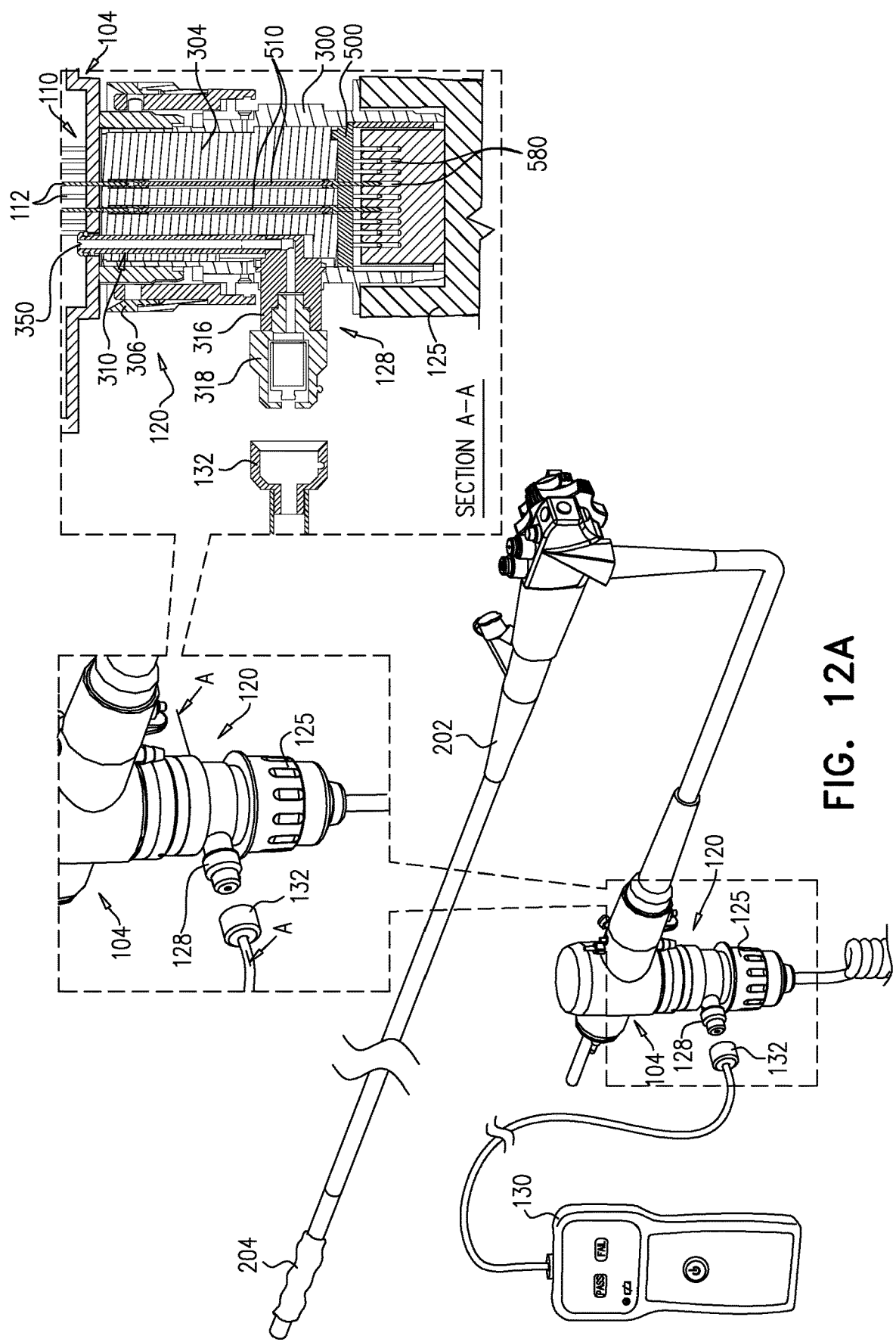
FIGS. 12A and 12B are simplified illustrations showing two operative orientations of the electro-pneumatic adaptor of FIGS. 3A-3C when connected to the leak testing subsystem forming part of the balloon endoscope system of FIG. 2A.
Figure 12B:
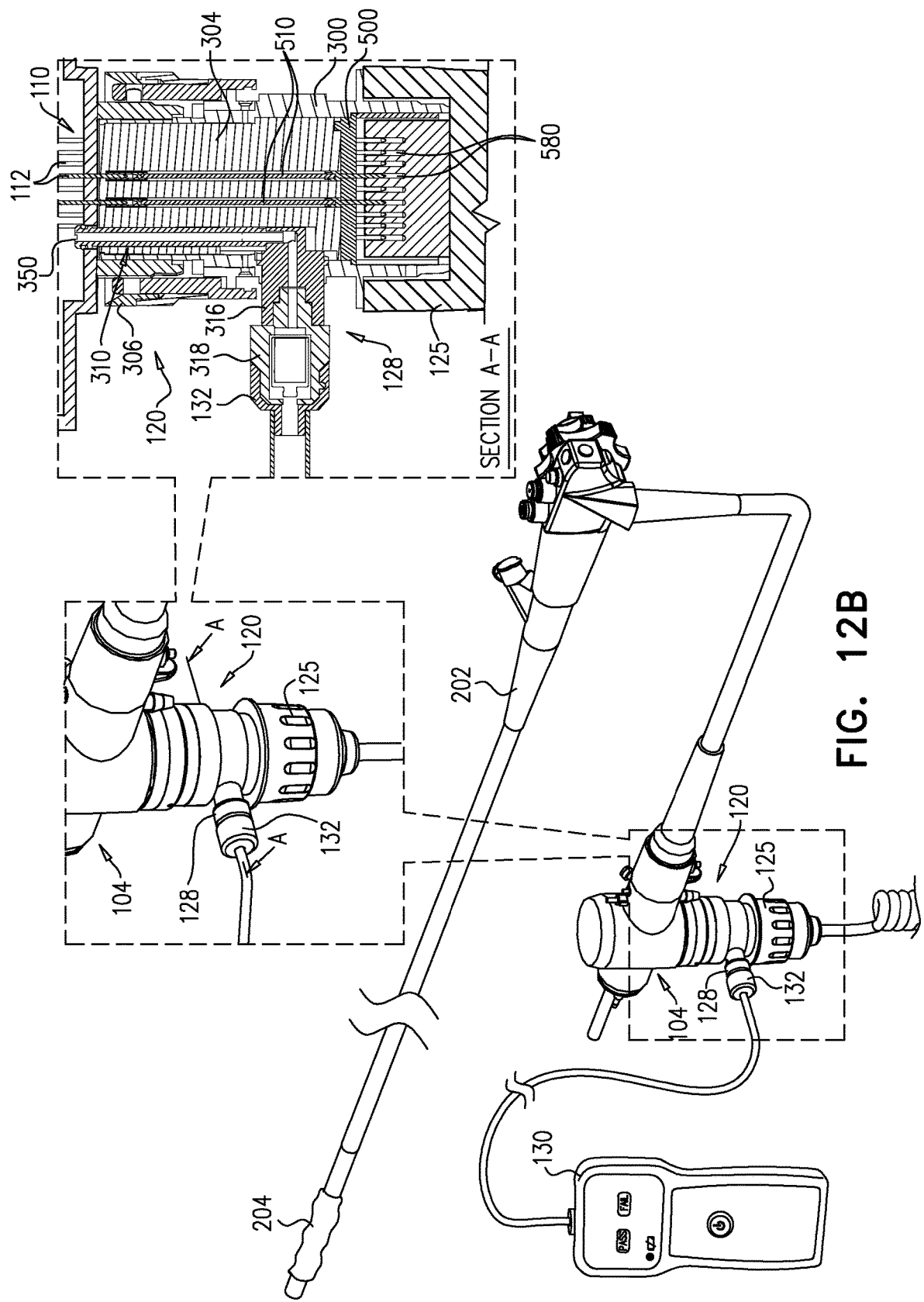

Reference is now made FIGS. 12A and 12B, which are simplified illustrations showing two operative orientations of the electro-pneumatic adaptor of FIGS. 3A-3C relative to the leak testing subsystem forming part of the balloon endoscope system of FIG. 2A. In FIG. 12A, it is seen that the electro-pneumatic adaptor 120 is connected to the balloon endoscope 202 and to electro-optic subsystem 126 via connector 125 (FIG. 1) but is entirely disconnected from leak testing subsystem 130.

In FIG. 12B, it is seen that second pneumatic connector element 318 is connected to leak testing subsystem 130 via connector 132, which preferably is bayonet connected to second pneumatic connector element 318 in a conventional manner.

Figure 13A:
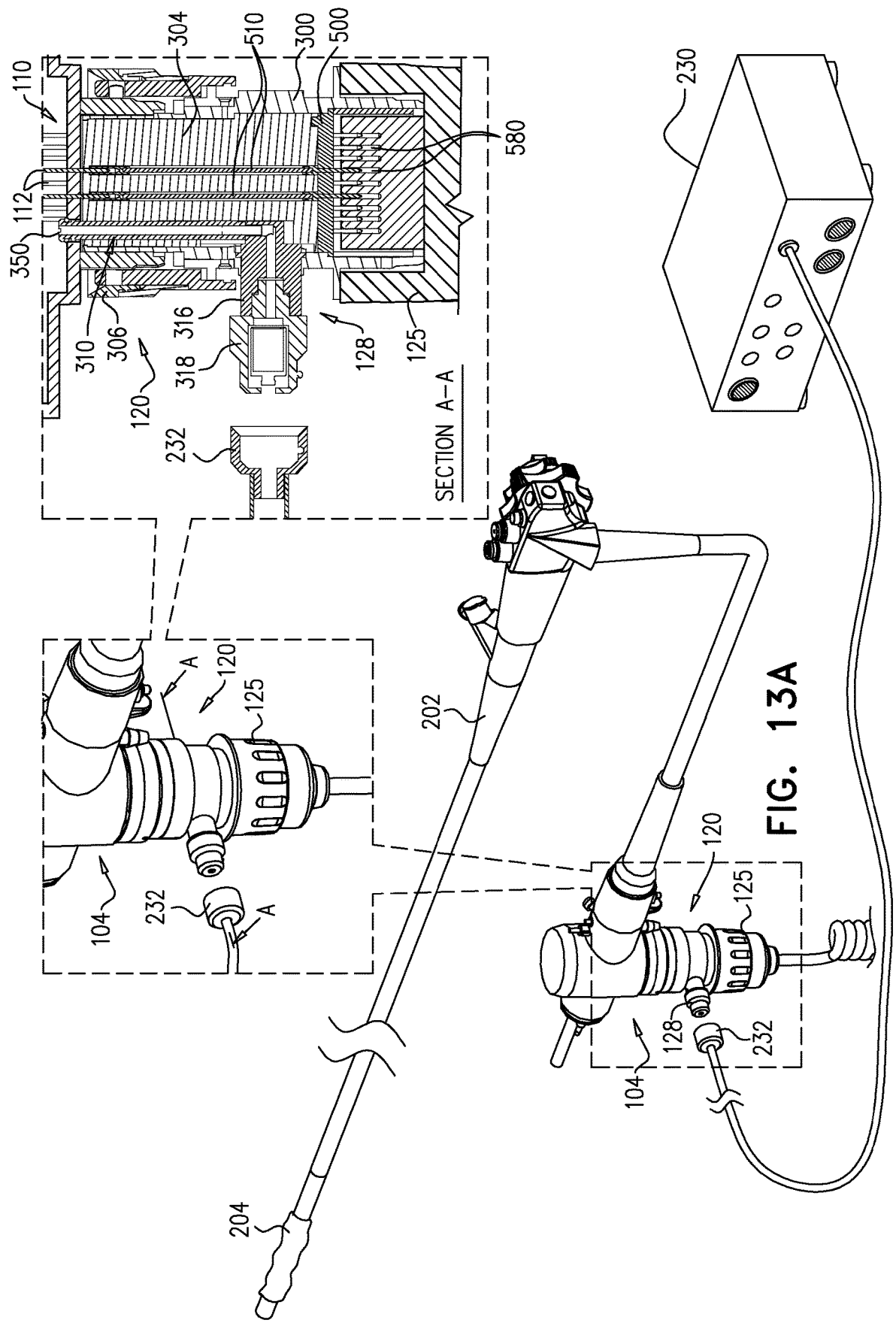
FIGS. 13A and 13B are simplified illustrations showing two operative orientations of the electro-pneumatic adaptor of FIGS. 3A-3C relative to the inflation/deflation subsystem forming part of the balloon endoscope system of FIG. 2B.
Figure 13B:
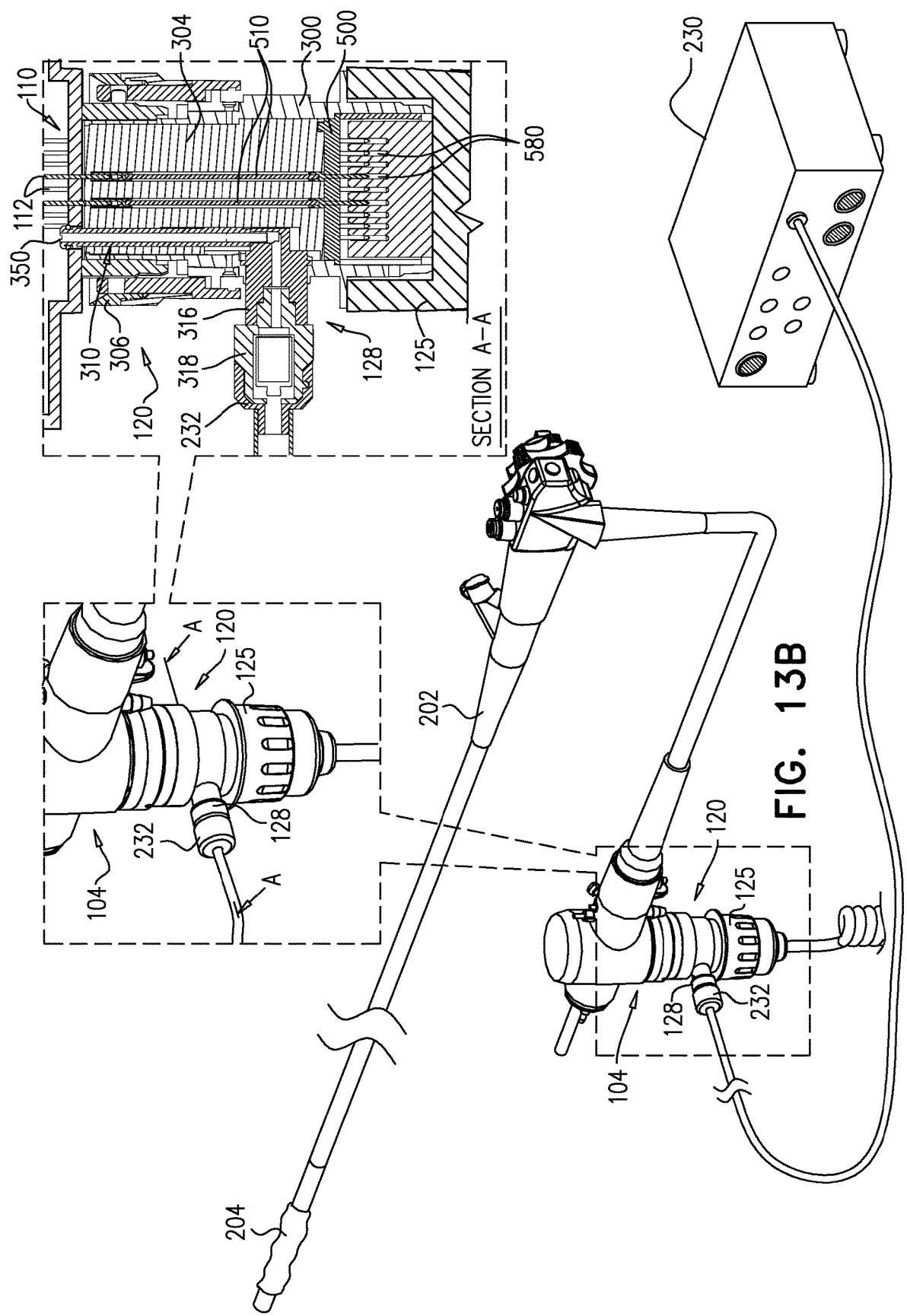

Reference is now made to FIGS. 13A and 13B, which are simplified illustrations showing two operative orientations of the electro-pneumatic adaptor of FIGS. 3A-3C relative to the inflation/deflation subsystem 230 forming part of the balloon endoscope system of FIG. 2B. In FIG. 13A, it is seen that the electro-pneumatic adaptor 120 is connected to the balloon endoscope 202 and to electro-optic subsystem 126 via connector 125 (FIG. 1) but is entirely disconnected from inflation/deflation subsystem 230 and from connector 232.

In FIG. 13B, it is seen that second pneumatic connector element 318 is connected to inflation/deflation subsystem 230 via connector 232, which preferably is bayonet connected to second pneumatic connector element 318 in a conventional manner.

It will be appreciated by persons skilled in the art that the scope of the present invention is not limited by what has been particularly shown and described hereinabove. Rather the scope of the present invention includes the combinations and subcombinations of the features described hereinabove as well as modifications thereof which are not in the prior art.

The invention claimed is:

1. An endoscope system comprising:
    an endoscope including an endoscope electro-pneumatic connection assembly having a leak test port;
    an endoscope electro-optic subsystem which is connectable to said endoscope via said endoscope electro-pneumatic connection assembly in a manner which precludes access to said leak test port when said endoscope electro-optic subsystem and said endoscope are directly connected at said electro-pneumatic connection assembly; and
    an electro-pneumatic adaptor being connectable to said endoscope at said electro-pneumatic connection assembly and comprising:
        a plurality of adaptor connectors, including an electrical connector for connection to an electrical connector of said endoscope, a pneumatic connector portion for connection to a pneumatic connector portion of said endoscope electro-pneumatic connection assembly, and a leak test port connector for connection to said leak test port of said endoscope,
        an adaptor electrical port connector to which said endoscope electro-optic subsystem is connectable, and
        a pneumatic connector assembly with a pneumatic conduit pneumatically connecting said pneumatic connector assembly to said leak test port connector.

2. An endoscope system according to claim 1 and wherein said leak test port communicates with an interior volume of said endoscope.

3. An endoscope system according to claim 1 and wherein:
    said endoscope is a balloon endoscope; and
    said pneumatic connector assembly of said electro-pneumatic adaptor is connected to a balloon inflation/deflation subsystem.

4. An endoscope system according to claim 3 and wherein said balloon inflation/deflation subsystem is adapted to provide inflation and deflation of said balloon via said pneumatic connector assembly of said adaptor, said leak test port and an interior volume of said endoscope.

5. An endoscope system according to claim 1 and wherein said electro-pneumatic adaptor is constructed such that said plurality of adaptor connectors, said adaptor electrical port assembly and said pneumatic connector assembly are directed at mutually different angles.

6. An endoscope system according to claim 1 and wherein said pneumatic connector assembly is fixedly connected to at least one of a leak tester and a balloon inflation/deflation subsystem.

7. An endoscope system according to claim 1 and wherein said pneumatic connector assembly of said electro-pneumatic adaptor is connected to a leak tester.

8. An endoscope system according to claim 3 and wherein said pneumatic connector assembly is removably connected to said balloon inflation/deflation subsystem.

* * * * *